United States Patent
Castro et al.

(10) Patent No.: US 10,492,769 B2
(45) Date of Patent: Dec. 3, 2019

(54) ORAL RETRACTION DEVICES AND METHODS

(71) Applicant: Medrobotics Corporation, Raynham, MA (US)

(72) Inventors: Michael Castro, Plymouth, MA (US); Joseph Karcsmar, Raynham, MA (US); R. Maxwell Flaherty, Auburndale, FL (US); J. Christopher Flaherty, Auburndale, FL (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 15/038,531

(22) PCT Filed: Nov. 24, 2014

(86) PCT No.: PCT/US2014/067091
§ 371 (c)(1),
(2) Date: May 23, 2016

(87) PCT Pub. No.: WO2015/081008
PCT Pub. Date: Jun. 4, 2015

(65) Prior Publication Data
US 2016/0287224 A1 Oct. 6, 2016

Related U.S. Application Data

(60) Provisional application No. 61/909,605, filed on Nov. 27, 2013, provisional application No. 61/921,858, (Continued)

(51) Int. Cl.
*A61B 1/32* (2006.01)
*A61B 13/00* (2006.01)
(Continued)

(52) U.S. Cl.
CPC .......... *A61B 13/00* (2013.01); *A61B 17/0206* (2013.01); *A61B 17/24* (2013.01); *A61B 2217/005* (2013.01); *A61B 2217/007* (2013.01)

(58) Field of Classification Search
CPC ..... A61B 17/02–17/0293; A61B 13/00; A61B 1/24
See application file for complete search history.

(56) References Cited

U.S. PATENT DOCUMENTS

| 1,388,170 A | 8/1921 | Cameron |
| 3,550,584 A | 12/1970 | Ring |

(Continued)

FOREIGN PATENT DOCUMENTS

| JP | 58191007 | 12/1983 |
| JP | 05076545 | 3/1993 |
| WO | 2012167043 | 12/2012 |

OTHER PUBLICATIONS

ISWRO dated Mar. 17, 2015 in corresponding International Application No. PCT/US2014/067091
(Continued)

*Primary Examiner* — Eduardo C Robert
*Assistant Examiner* — Steven J Cotroneo
(74) *Attorney, Agent, or Firm* — Onello & Mello, LLP.

(57) ABSTRACT

An oral retraction device comprises a tongue depressor blade, an articulation assembly constructed and arranged to articulate the tongue depressor blade with at least three degrees of freedom, and a support element constructed and arranged to provide a stabilizing force to the articulation assembly during articulation of the tongue depressor blade.

13 Claims, 12 Drawing Sheets

Related U.S. Application Data filed on Dec. 30, 2013, provisional application No. 62/008,453, filed on Jun. 5, 2014, provisional application No. 62/052,736, filed on Sep. 19, 2014.

(51) Int. Cl.
*A61B 17/02* (2006.01)
*A61B 17/24* (2006.01)

(56) References Cited

U.S. PATENT DOCUMENTS

| | | | | |
|---|---|---|---|---|
| 4,024,859 | A | * | 5/1977 | Slepyan .................... A61B 1/24 600/215 |
| 4,148,308 | A | | 4/1979 | Sayer |
| 5,897,491 | A | * | 4/1999 | Kastenbauer ............ A61B 1/24 600/237 |
| 7,887,483 | B2 | * | 2/2011 | Rosenberg ............. A61B 90/14 600/223 |
| 8,864,661 | B2 | | 10/2014 | Olsen |
| 9,339,176 | B2 | | 5/2016 | Weinstein et al. |
| 2008/0114209 | A1 | * | 5/2008 | Cohen ................. A61B 17/0206 600/210 |
| 2008/0319720 | A1 | | 12/2008 | Ellis et al. |
| 2009/0105547 | A1 | * | 4/2009 | Vayser ............... A61B 17/0206 600/228 |
| 2009/0203969 | A1 | * | 8/2009 | Cohen .................... A61B 17/02 600/245 |
| 2010/0217089 | A1 | * | 8/2010 | Farley .................... A61B 17/02 600/213 |
| 2010/0256454 | A1 | * | 10/2010 | Farley .................... A61B 17/02 600/210 |
| 2012/0157787 | A1 | | 6/2012 | Weinstein et al. |
| 2013/0296654 | A1 | * | 11/2013 | Olsen ................. A61B 17/0293 600/205 |
| 2014/0005683 | A1 | | 1/2014 | Stand et al. |
| 2014/0012288 | A1 | | 1/2014 | Darisse et al. |
| 2014/0046305 | A1 | | 2/2014 | Castro et al. |
| 2014/0094825 | A1 | | 4/2014 | Flaherty et al. |
| 2014/0318299 | A1 | | 10/2014 | Oyola et al. |
| 2014/0371764 | A1 | | 12/2014 | Oyola et al. |

OTHER PUBLICATIONS

Extended European Search Report dated Oct. 13, 2017, issued in Application No. EP 14866536.7.

Chinese Office Action dated Apr. 24, 2018 issued in corresponding Chinese Application No. 201480074175.5, with English language summary.

Japanese Office Action dated Aug. 21, 2018 issued in corresponding Japanese Application No. 2016-535033, with English summary.

Australian Office Action dated Oct. 19, 2018 issued in corresponding Australian Application No. 2014354929.

Japanese Notice of Allowance dated Jan. 15, 2019 issued in corresponding Japanese Application No. 2016535033, with machine translation to English.

Chinese Office Action dated Jan. 11, 2019 issued in corresponding Chinese Application No. 201480074175.5, with machine translation to English.

* cited by examiner

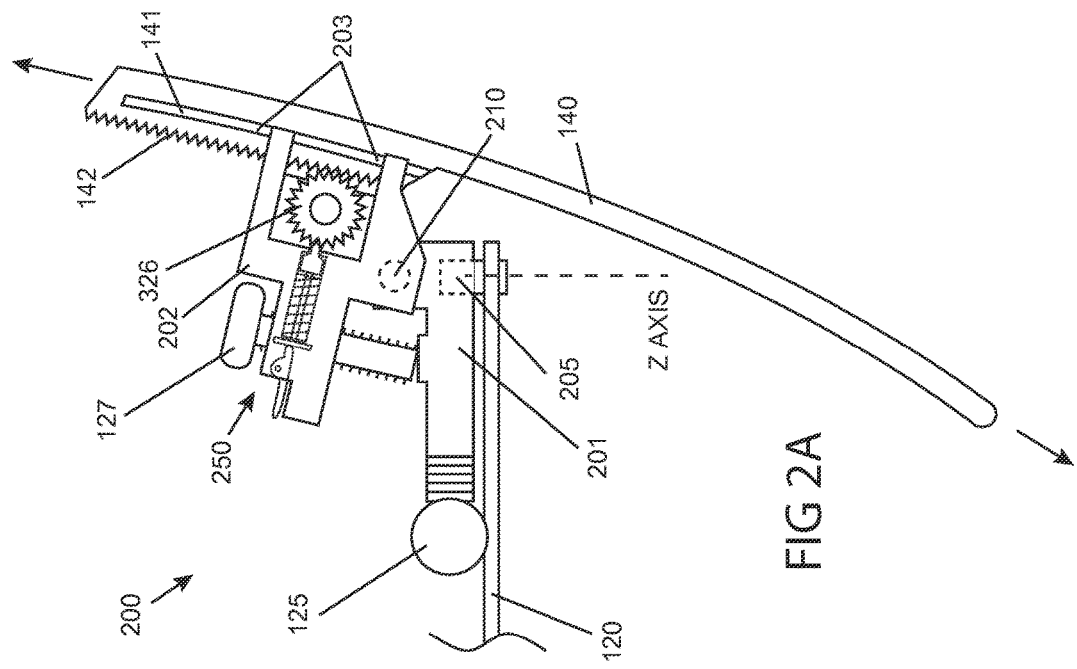
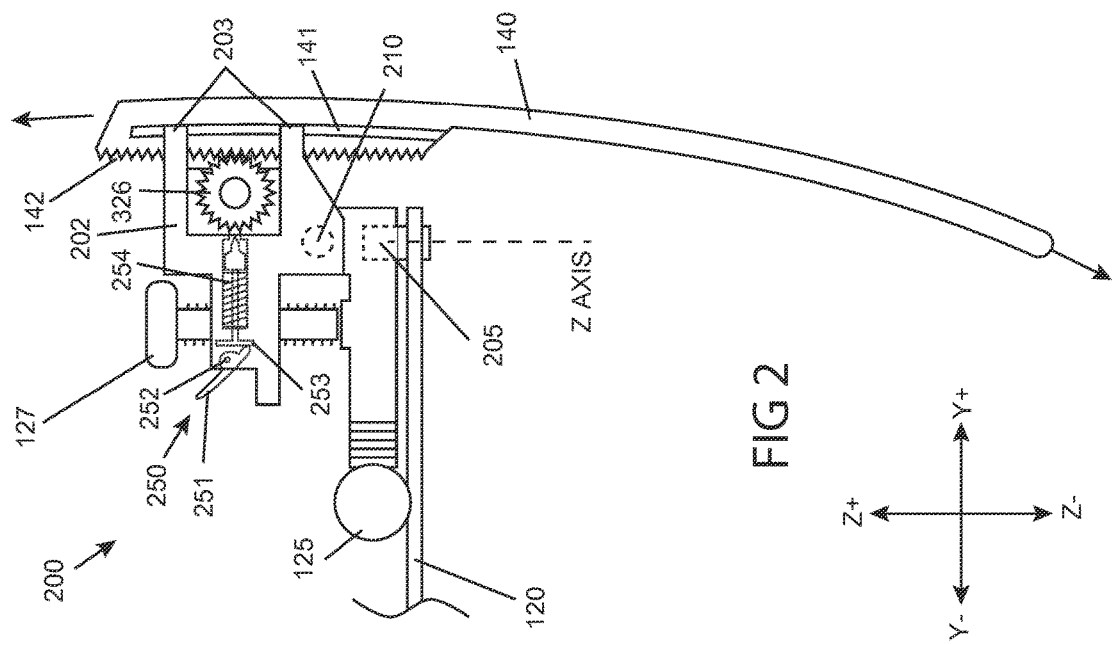

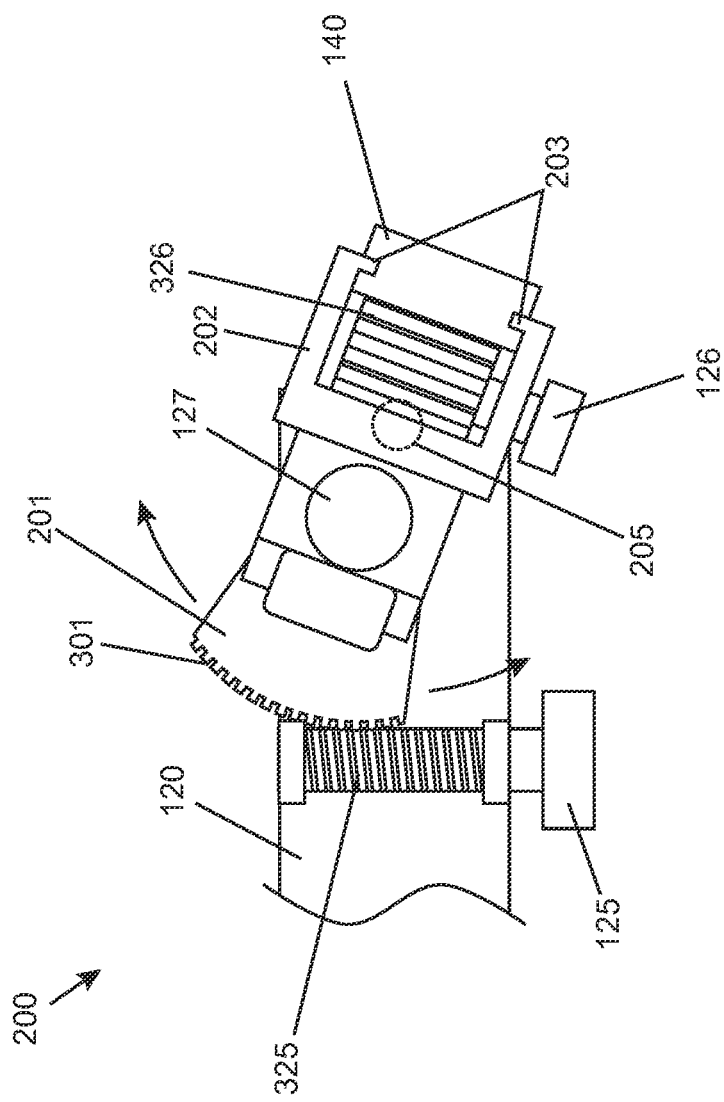
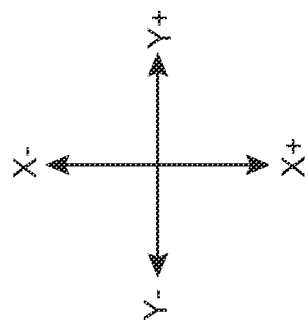
FIG 2B

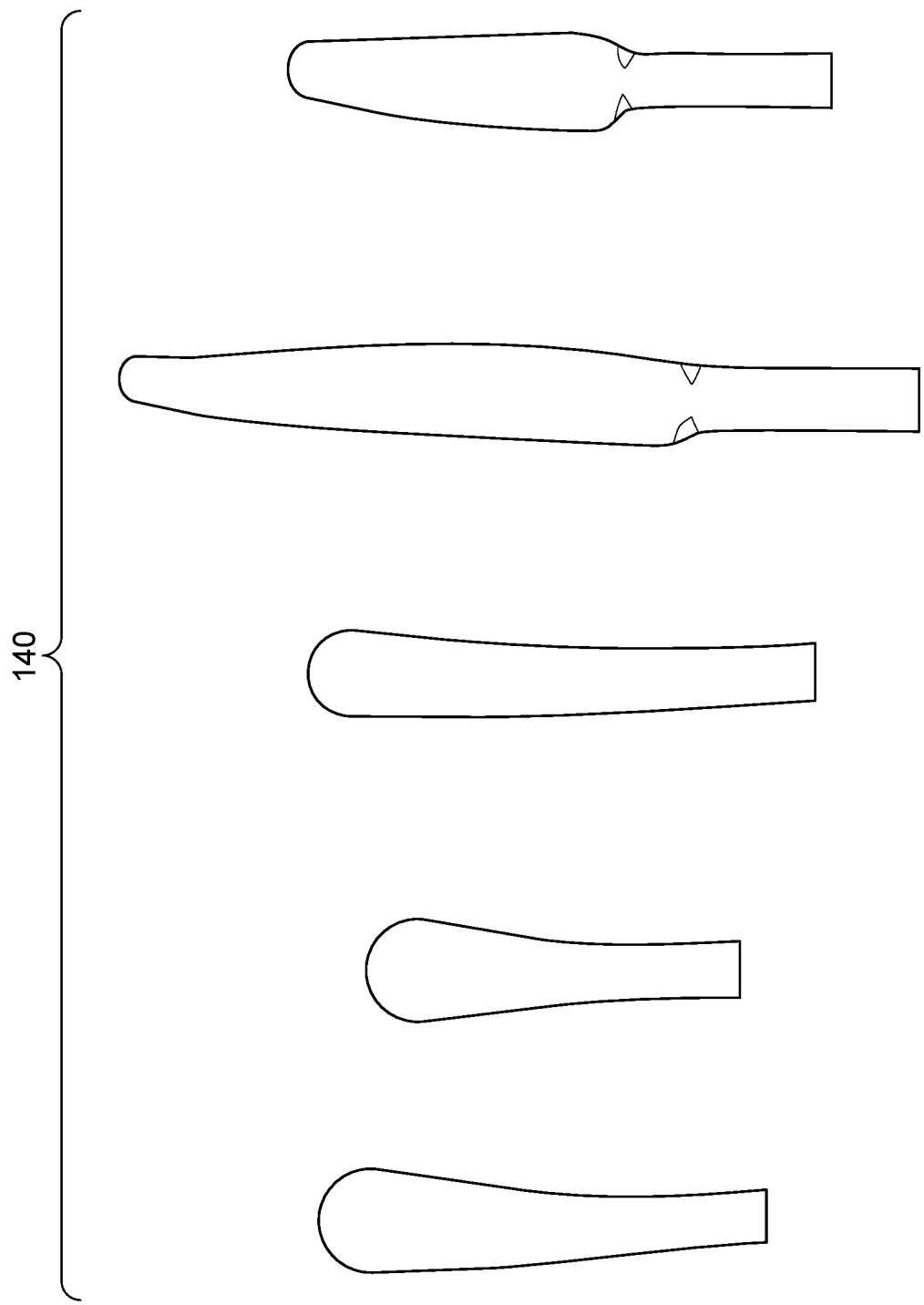

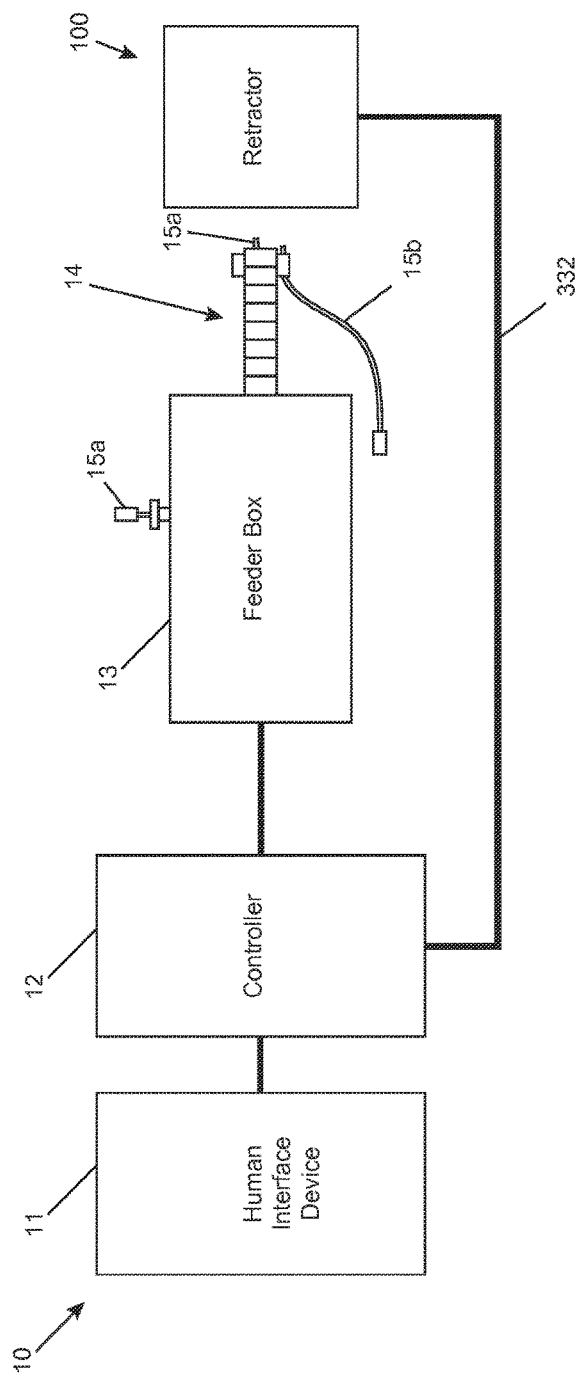
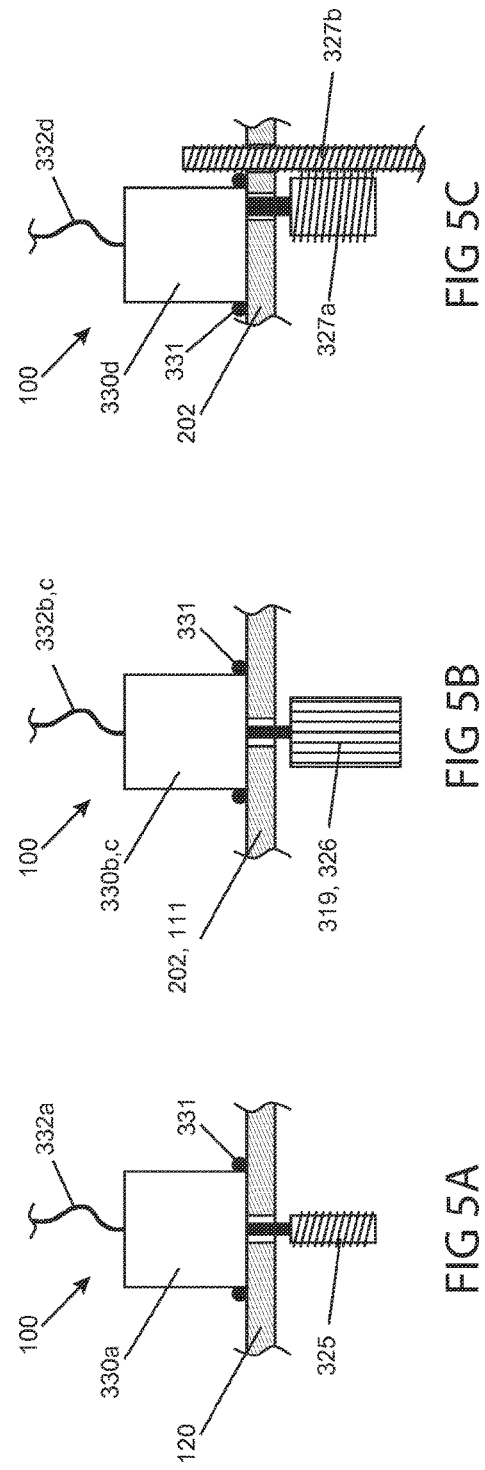
FIG 5
FIG 5A
FIG 5B
FIG 5C

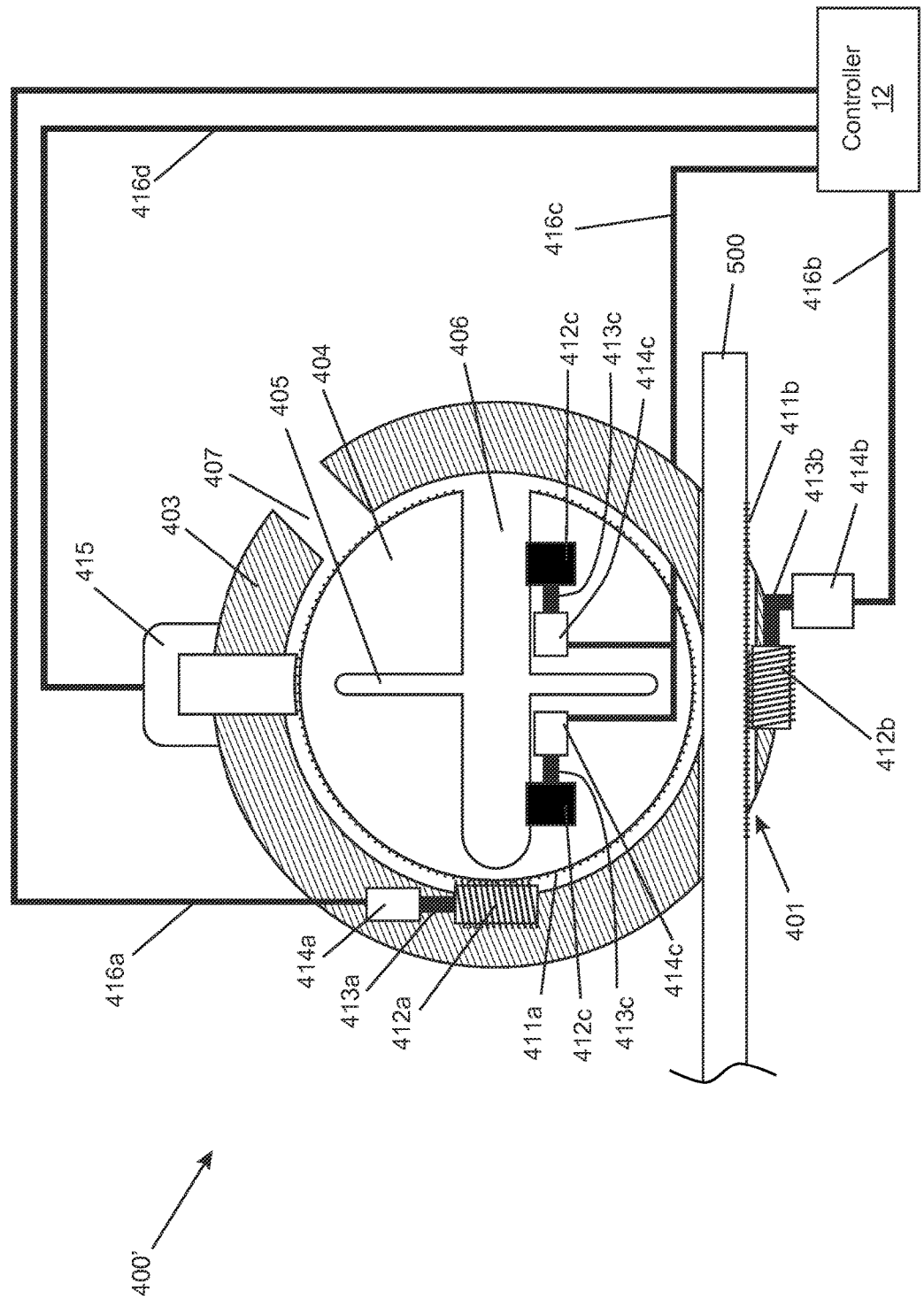

ORAL RETRACTION DEVICES AND METHODS

RELATED APPLICATIONS

This application claims the benefit of U.S. Provisional Application No. 61/921,858, filed Dec. 30, 2013, the content of which is incorporated herein by reference in its entirety This application claims the benefit of U.S. Provisional Application No. 61/909,605, filed Nov. 27, 2013, the content of which is incorporated herein by reference in its entirety.

This application claims the benefit of U.S. Provisional Application No. 62/052,736, filed Sep. 19, 2014, the content of which is incorporated herein by reference in its entirety.

This application claims the benefit of U.S. Provisional Application No. 62/008,453, filed Jun. 5, 2014, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. patent application Ser. No. 13/880,525, filed Apr. 19, 2013, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No. PCT/US12/40414, filed Jun. 1, 2012, the content of which is incorporated herein by reference in its entirety.

This application is related to U.S. patent application Ser. No. 14/119,316, filed Nov. 21, 2013, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2011/060214, filed Nov. 10, 2011, the content of which is incorporated herein by reference in its entirety.

This application is related to U.S. patent application Ser. No. 13/884,407, filed May 9, 2013, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No. PCT/US12/32279, filed Apr. 5, 2012, the content of which is incorporated herein by reference in its entirety.

This application is related to U.S. patent application Ser. No. 14/008,775, filed Sep. 30, 2013, the content of which is incorporated herein by reference in its entirety.

This application is related to U.S. Provisional Application No. 61/534,032 filed Sep. 13, 2011, the content of which is incorporated herein by reference in its entirety.

This application is related to PCT Application No. PCT/US12/54802, filed Sep. 12, 2012, the content of which is incorporated herein by reference in its entirety.

This application is related to U.S. patent application Ser. No. 14/343,915, filed Mar. 10, 2014, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 13/812,324, filed Jan. 25, 2013, the content of which is incorporated herein by reference in its entirety.

This application is related to U.S. Provisional Application No. 61/578,582, filed Dec. 21, 2011, the content of which is incorporated herein by reference in its entirety.

This application is related to PCT Application No. PCT/US12/70924, filed Dec. 20, 2012, the content of which is incorporated herein by reference in its entirety.

This application is related to U.S. patent application Ser. No. 14/364,195, filed Jun. 10, 2014, the content of which is incorporated herein by reference in its entirety.

This application is related to U.S. Provisional Application No. 61/681,340, filed Aug. 9, 2012, the content of which is incorporated herein by reference in its entirety.

This application is related to PCT Application No. PCT/US13/54326, filed Aug. 9, 2013, the content of which is incorporated herein by reference in its entirety.

This application is related to U.S. Provisional Application No. 61/751,498, filed Jan. 11, 2013, the content of which is incorporated herein by reference in its entirety.

This application is related to PCT Application No. PCT/US14/01808, filed Jan. 9, 2014, the content of which is incorporated herein by reference in its entirety.

This application is related to U.S. Provisional Application No. 61/656,600, filed Jun. 7, 2012, the content of which is incorporated herein by reference in its entirety.

This application is related to PCT Application No. PCT/US13/43858, filed Jun. 3, 2013, the content of which is incorporated herein by reference in its entirety.

This application is related to U.S. patent application Ser. No. 14/402,224, filed Nov. 19, 2014, the content of which is incorporated herein by reference in its entirety.

This application is related to U.S. Provisional Application No. 61/825,297, filed May 20, 2013, the content of which is incorporated herein by reference in its entirety.

This application is related to PCT Application No. PCT/US13/38701, filed May 20, 2014, the content of which is incorporated herein by reference in its entirety.

This application is related to U.S. Provisional Application No. 61/818,878, filed May 2, 2013, the content of which is incorporated herein by reference in its entirety.

This application is related to PCT Application No. PCT/US14/36571, filed May 2, 2014, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

The present inventive concepts generally relate to the field of surgical instruments, and more particularly, to oral retractors.

BACKGROUND

As less invasive medical techniques and procedures become more widespread, medical professionals, such as surgeons, may require articulating surgical tools, such as endoscopes, to perform such less invasive medical techniques and procedures that access interior regions of the body via a body orifice such as the mouth. A mouth retractor is typically used to hold the mouth open, and to retract the tongue, lips, and cheeks so that the throat, and interior regions proximal to the throat, can be accessed by a surgical tool.

SUMMARY

In one aspect, provided is an oral retraction device comprising a tongue depressor blade; an articulation assembly constructed and arranged to articulate the tongue depressor blade with at least three degrees of freedom; and a support element constructed and arranged to provide a stabilizing force to the articulation assembly during articulation of the tongue depressor blade.

In some embodiments, the oral retraction device is positioned in a mouth region of a patient, and is constructed and arranged to provide access via the mouth region to an interior region of the patient.

In some embodiments, the interior region comprises at least one of a nasal passage, throat, oropharynx, esophagus, vocal chords, stomach, and/or to directly or indirectly access regions of the body proximal to the nasal passage, throat, oropharynx, esophagus, vocal chords, or stomach of the patient.

In some embodiments, the oral retraction device is used to introduce an articulating robotic probe to at least the mouth region of the patient.

In some embodiments, the oral retraction device, when in a stabilization state, applies a force to the mouth region to control a geometry of the patient's mouth region.

In some embodiments, the oral retraction device applies the force to at least one of the lips, tongue, teeth, or cheeks of the mouth region.

In some embodiments, the force is applied to the mouth region to minimize or avoid re-positioning of the patient's head prior to or during a medical procedure.

In some embodiments, an articulation or geometric modification of one or more elements of the oral retraction device is performed according to a one-handed operation.

In some embodiments, the oral retraction device is positioned in a patient's mouth and a force is applied to the patient's tongue by the tongue depressor blade to provide access to an internal location of the patient during one or more medical procedures.

In some embodiments, the tongue depressor blade is removably coupled to the articulation assembly.

In some embodiments, the tongue depressor blade is removable from the articulation assembly while the oral retraction device is positioned in the patient's mouth.

In some embodiments, the tongue depressor blade is removable according to a one-handed operation.

In some embodiments, the support element comprises a support will coupled to a linear positioning assembly, the linear positioning assembly articulating the support element in a linear direction.

In some embodiments, the support element comprises a frame coupled to a linear positioning assembly, the linear positioning assembly articulating the support element in a linear direction.

In some embodiments, the support element comprises a first support element slidingly coupled to one portion of a linear positioning assembly, and a second support element fixedly coupled to another portion of the linear positioning assembly, the first support element comprising a support arm, the second support element comprising a frame, the linear positioning assembly articulating the support element in a linear direction.

In some embodiments, the frame moves relative to the support arm in response to a linear translation of the linear positioning assembly.

In some embodiments, the support arm and the frame provide a supporting force at both ends of the oral retraction device.

In some embodiments, the support arm further comprises an attachment portion constructed and arranged to attach to a support structure at one end of the oral retraction device for providing the stabilizing force.

In some embodiments, the attachment portion partially surrounds a tubular portion of the support structure or otherwise engages the support structure to stabilize and/or maintain the position of the support arm.

In some embodiments, the support structure comprises a support rod coupled to a stable structure.

In some embodiments, the support arm comprises a handle constructed and arranged to be stabilized by an operator.

In some embodiments, the operator uses the handle to stabilize the oral retraction device at a patient's mouth.

In some embodiments, the frame extends in a direction of extension along an axis, and a translation of the frame relative to the support arm along the axis applies an opening force to a patient's mouth along the axis.

In some embodiments, the oral retraction device further comprises a plurality of cheek retractors and a plurality of molar supports coupled to a frame of the support element.

In some embodiments, one or more forces are applied to the patient's cheeks by at least one cheek retractor of the plurality of cheek retractors.

In some embodiments, one or more forces are applied to the patient's teeth by the at least one of the molar supports.

In some embodiments, the frame includes a cheek positioning slot corresponding to each of the cheek retractors and a molar adjustment slot corresponding to each of the molar supports.

In some embodiments, the cheek positioning slot is constructed and arranged for positioning the cheek retractors along a portion of the frame extending along a first axis, and wherein the molar adjustment slots are constructed and arranged for positioning the molar supports along a portion of the frame extending along a second axis orthogonal to the first axis.

In some embodiments, the molar supports provide a resistive force for the frame such that the translation of a support arm at an opposite end of the oral retraction device as the frame along the first axis spreads open the patient's mouth along the first axis, and wherein the cheek retractors provide a resistive force to spread the patient's mouth open along the second axis.

In some embodiments, at least one of the molar supports or the cheek retractors is removably coupled to the frame.

In some embodiments, the molar supports are adjustable with respect to their position on the frame to accommodate a location of a patient's molar teeth.

In some embodiments, the frame includes a molar adjustment arch, wherein the molar adjustment slots are at the molar adjustment arch, and wherein the molar adjustment arch is configured so that the molar supports are aligned with the patient's molar teeth or other teeth or portion of the upper jaw of the patient.

In some embodiments, the articulation assembly comprises a linear positioning assembly that articulates a frame of the support element in a linear direction relative to a support arm of the support element.

In some embodiments, a movement of the linear positioning assembly allows an operator-generated translation of the frame to change the distance between molar supports coupled to the frame and the tongue depressor blade.

In some embodiments, the linear positioning assembly is constructed and arranged to limit translation in one or more directions, and to maintain the linear positioning assembly in a series of linear positions.

In some embodiments, the linear positioning assembly comprises a base having an end at which the frame is coupled and a ratchet assembly that controls a translation of the linear positioning assembly along a first axis.

In some embodiments, the ratchet assembly comprises a lever having a ratchet locking portion, and further comprising a spring assembly, wherein the ratchet assembly is biased by the spring assembly.

In some embodiments, the lever and the locking portion are constructed and arranged to enable one of the degrees of freedom and to allow a translation of the linear positioning assembly in a linear direction under the control of the ratchet assembly, and wherein an activation of the lever and the locking portion prevents movement of the linear positioning assembly in at least one direction along the first axis and disables the one of the degrees of freedom.

In some embodiments, when a force is applied to a proximal end of the lever, the locking portion is disengaged, permitting the linear positioning assembly to freely move along the first axis.

In some embodiments, the ratchet assembly is configured to allow a rapid release of force applied to the patient's molars in response to applying a force to the lever, such as to allow rapid removal of the oral retraction device from the patient's mouth.

In some embodiments, the support arm comprises a set of teeth, and the linear positioning assembly includes a gear which operatively engages the teeth, and wherein in a first, engaged position, the ratchet locking portion engages the teeth, and wherein in a second, disengaged position, the ratchet locking portion disengages from the teeth, allowing the translating assembly to move freely.

In some embodiments, the gear is attached to a linear positioning knob such that a rotation of linear positioning knob translates to a rotation of the gear about its axis and subsequent linear translation of the linear positioning assembly with respect to the support element.

In some embodiments, the articulation assembly is constructed and arranged to rotationally articulate the tongue depressor blade.

In some embodiments, the articulation assembly includes a multi-axis gear assembly and a plurality of knobs that articulate the tongue depressor blade in the at least three degrees of freedom.

In some embodiments, the knobs include at least one of a rotational positioning knob, a height positioning knob, or an angular positioning knob.

In some embodiments, a rotation of the angular positioning knob drives an articulation of the tongue depressor blade in a curvilinear direction with a single degree of freedom about a first axis.

In some embodiments, a rotation of the height positioning knob drives an articulation of the tongue depressor blade in a linear direction with a single degree of freedom relative to a second axis orthogonal to the first axis for adjusting an insertion length of the tongue depressor blade.

In some embodiments, a rotation of the rotational positioning knob drives an articulation of the tongue depressor blade in a curvilinear direction with a single degree of freedom about a third axis orthogonal to the first and second axes.

In some embodiments, an engagement of a combination of one or more of the rotational positioning knob, the height positioning knob, and the angular positioning knob permits access to a mouth region of a patient.

In some embodiments, additional degrees of freedom can be achieved through a rotation of the linear positioning knob which in turn causes a translation of a frame in communication with the linear positioning assembly.

In some embodiments, the linear positioning knob is rotated to adjust the force applied to the patient's teeth thereby adjusting the opening through the mouth by changing the distance between a frame in communication with the linear positioning assembly relative to the tongue depressor blade.

In some embodiments, a single handed adjustment of the frame can be achieved by applying a force to at least one of the linear positioning knob or a ratchet assembly lever.

In some embodiments, the oral retraction device further comprises a tool for positioning about at least one of the plurality of knobs.

In some embodiments, the tool is constructed and arranged to be gripped by one or more fingers of an operator's hand in rotating the engaged at least one of the plurality of knobs.

In some embodiments, the tool is constructed and arranged to be coupled to a motor for rotating the engaged at least one of the plurality of knobs.

In some embodiments, a single handed adjustment of the tongue depressor blade is achieved by turning at least one of the knobs.

In some embodiments, the articulation assembly comprises a first portion and a second portion in communication with the first portion, and wherein the first portion articulates relative to a support arm of the support element.

In some embodiments, the oral retraction device further comprises an axle extending from the support arm, the first portion positioned about the axle for rotating about the axle.

In some embodiments, a rotation of a rotational positioning knob drives an articulation of the first portion about the axle.

In some embodiments, the second portion of the articulation assembly is configured to rotate relative to the first portion.

In some embodiments, an angular positioning knob is configured to act as a stop lock when the second portion rotates about the axle.

In some embodiments, the second portion comprises one or more arms configured to abut and slidingly receive the tongue depressor blade via a channel.

In some embodiments, the tongue depressor blade comprises a set of geared teeth configured to frictionally engage a gear of a multi-axis gear assembly coupled to an axle that extends along an axis.

In some embodiments, the gear is coupled to a height positioning knob, and rotates about its axle in response to a rotation of the height positioning knob, and wherein the rotation of the gear engages the geared teeth, which in turn moves the tongue depressor blade via the channel along a linear path thereby adjusting a vertical position of the tongue depressor blade relative to the arms of the articulation assembly.

In some embodiments, the height positioning knob causes the tongue depressor blade to translate vertically.

In some embodiments, the articulation assembly comprises a locking assembly that is constructed and arranged to, when in a locked position, lock the horizontal position of tongue depressor, and in an unlocked position, allow for an adjustment of the depth position of tongue depressor blade.

In some embodiments, the locking assembly comprises a lever configured as a quick release mechanism such as a mechanism released via a single finger or single hand of an operator.

In another aspect, provided is a method for performing a medical procedure using a surgical instrument in accordance with embodiments herein.

In another aspect, provided is an oral retraction device, comprising a tongue depressor blade; an articulation assembly constructed and arranged to rotationally articulate the tongue depressor blade; and a support element constructed and arranged to provide a stabilizing force to the articulation assembly during articulation of the tongue depressor blade.

In some embodiments, the oral retraction device is positioned in a mouth region of a patient, and is constructed and arranged to provide access via the mouth region to an interior region of the patient.

In some embodiments, an articulation or geometric modification of one or more elements of the oral retraction device is performed according to a one-handed operation.

In some embodiments, the support element comprises a support arm coupled to a linear positioning assembly, the linear positioning assembly articulating the support element in a linear direction.

In some embodiments, the support element comprises a frame coupled to a linear positioning assembly, the linear positioning assembly articulating the support element in a linear direction.

In some embodiments, the support element comprises a first support element slidingly coupled to one portion of a linear positioning assembly, and a second support element fixedly coupled to another portion of the linear positioning assembly, the first support element comprising a support arm, the second support element comprising a frame, the linear positioning assembly articulating the support element in a linear direction.

In some embodiments, the support element further comprises an attachment portion constructed and arranged to attach to a support structure at one end of the oral retraction device for providing the stabilizing force.

In some embodiments, the oral retraction device further comprises a plurality of cheek retractors and a plurality of molar supports coupled to a frame of the support element.

In some embodiments, the frame includes a cheek positioning slot corresponding to each of the cheek retractors and a molar adjustment slot corresponding to each of the molar supports.

In some embodiments, the cheek positioning slot is constructed and arranged for positioning the cheek retractors along a portion of the frame extending along a first axis, and wherein the molar adjustment slots are constructed and arranged for positioning the molar supports along a portion of the frame extending along a second axis orthogonal to the first axis.

In some embodiments, the molar supports provide a resistive force for the frame such that the translation of a support arm at an opposite end of the oral retraction device as the frame along the first axis spreads open the patient's mouth along the first axis, and wherein the cheek retractors provide a resistive force to spread the patient's mouth open along the second axis.

In some embodiments, at least one of the molar supports or the cheek retractors is removably coupled to the frame.

In some embodiments, the molar supports are adjustable with respect to their position on the frame to accommodate a location of a patient's molar teeth.

In some embodiments, the articulation assembly comprises a linear positioning assembly that articulates a frame of the support element in a linear direction relative to a support arm of the support element.

In some embodiments, a movement of the linear positioning assembly allows an operator-generated translation of the frame to change the distance between molar supports coupled to the frame and the tongue depressor blade.

In some embodiments, the linear positioning assembly is constructed and arranged to limit translation in one or more directions, and to maintain the linear positioning assembly in a series of linear positions.

In some embodiments, the linear positioning assembly comprises a base having an end at which the frame is coupled and a ratchet assembly that controls a translation of the linear positioning assembly along a first axis.

In some embodiments, the ratchet assembly comprises a lever having a ratchet locking portion, and further comprising a spring assembly, wherein the ratchet assembly is biased by the spring assembly.

In some embodiments, the lever and the locking portion are constructed and arranged to enable one of the degrees of freedom and to allow a translation of the linear positioning assembly in a linear direction under the control of the ratchet assembly, and wherein an activation of the lever and the locking portion prevents movement of the linear positioning assembly in at least one direction along the first axis and disables the one of the degrees of freedom.

In some embodiments, the support arm comprises a set of teeth, and wherein the linear positioning assembly includes a gear which operatively engages the teeth, and wherein in a first, engaged position, the ratchet locking portion engages the teeth, and wherein in a second, disengaged position, the ratchet locking portion disengages from the teeth, allowing the translating assembly to move freely.

In some embodiments, the articulation assembly is constructed and arranged to rotationally articulate the tongue depressor blade.

In some embodiments, the articulation assembly includes a multi-axis gear assembly and a plurality of knobs that articulate the tongue depressor blade in the at least three degrees of freedom.

In some embodiments, the knobs include at least one of a rotational positioning knob, a height positioning knob, or an angular positioning knob.

In some embodiments, a rotation of the angular positioning knob drives an articulation of the tongue depressor blade in a curvilinear direction with a single degree of freedom about a first axis.

In some embodiments, a rotation of the height positioning knob drives an articulation of the tongue depressor blade in a linear direction with a single degree of freedom relative to a second axis orthogonal to the first axis for adjusting an insertion length of the tongue depressor blade.

In some embodiments, a rotation of the rotational positioning knob drives an articulation of the tongue depressor blade in a curvilinear direction with a single degree of freedom about a third axis orthogonal to the first and second axes.

In some embodiments, an engagement of a combination of one or more of the rotational positioning knob, the height positioning knob, and the angular positioning knob permits access to a mouth region of a patient.

In some embodiments, additional degrees of freedom are achieved through a rotation of the linear positioning knob which in turn causes a translation of a frame in communication with the linear positioning assembly.

In some embodiments, the linear positioning knob is rotated to adjust the force applied to the patient's teeth thereby adjusting the opening through the mouth by changing the distance between a frame in communication with the linear positioning assembly relative to the tongue depressor blade.

In some embodiments, a single handed adjustment of the frame can be achieved by applying a force to at least one of the linear positioning knob or a ratchet assembly lever.

In another aspect, provided is a method for performing a medical procedure using an oral retraction device in accordance with embodiments herein.

In another aspect, provided is a system, comprising a human interface device (HID); a controller; and a robotically manipulatable oral retractor, wherein the retractor includes an articulation assembly constructed and arranged to at least one of articulate a tongue depressor blade with at least three degrees of freedom or rotationally articulate the tongue depressor blade.

In some embodiments, the controller comprises a wire bundle including one or more wires or other power and/or signal carrying conduits, which are operably attached to the oral retractor.

In some embodiments, the HID comprises a user interface that allows an operator to send commands to control one or more portions of oral retractor via power and/or information by the controller via the wire bundle.

In some embodiments, an operator interfaces with the HID to adjust or otherwise control the retractor, such as to operate one or more controls of the retractor.

In some embodiments, the controls include at least one of a linear positioning motor, a rotational positioning motor, a height positioning motor, or an angular positioning motor of the oral retractor.

In one aspect, provided is a tool support comprises a cam comprising an opening for surrounding an elongate portion of a support device; an outer shell surrounding the cam; and a passageway for receiving a shaft portion of the medical device. The tool support is constructed and arranged to at least one of: translate the passageway along the support device elongate portion; or rotate the passageway about the support device elongate portion.

In some embodiments, the tool support is constructed and arranged to both translate along the support device elongate portion and rotate about the support device elongate portion.

In some embodiments, the tool support is pre-attached to the support device elongate portion.

In some embodiments, the tool support is constructed and arranged to be at least one of attachable or removable from the support device elongate portion. The tool support can be laterally attachable to the support device elongate portion.

In some embodiments, the cam comprises at least a portion of the passageway.

In some embodiments, the cam comprises a slot configured to be compressed and change the shape of the cam.

In some embodiments, the cam comprises at least a compressible portion. The compressible portion can comprise an elastomeric material.

In some embodiments, the cam is constructed and arranged to compress to frictionally the engage shaft portion of the medical device to the passageway. The tool support can further comprise a set screw and wherein rotation of the set screw compresses the cam. The frictional engagement of the shaft portion of the medical device to the passageway can prevent translation of the medical device within the passageway and/or prevent rotation of the medical device within the passageway.

In some embodiments, the cam is constructed and arranged to compress to frictionally engage the support device elongate portion with the tool support. The tool support can further comprise a set screw and wherein rotation of the set screw compresses the cam. The tool support can further comprise a set screw and wherein rotation of the set screw compresses the cam. The frictional engagement of the support device elongate portion can at least one of: prevent translation of the tool support along the support device or prevent rotation of the tool support about the support device.

In some embodiments, the cam opening comprises a non-circular opening.

In some embodiments, the support device elongate portion comprises a segment of a frame of a retractor device. The retractor device can comprise an oral retractor device as described herein.

In some embodiments, the outer shell comprises at least a portion of the passageway.

In some embodiments, the outer shell is constructed and arranged to rotate relative to the cam. The outer shell can be constructed and arranged to rotate at least 360°. The outer shell can be constructed and arranged to rotate less than 360°.

In some embodiments, the outer shell comprises an opening constructed and arranged to laterally receive the support device elongate portion as the tool support is attached to the support device.

In some embodiments, the outer shell is constructed and arranged to relatively maintain its shape during use.

In some embodiments, the passageway comprises a lumen positioned in the outer shell.

In some embodiments, the passageway comprises a lumen positioned in the cam.

In some embodiments, the passageway comprises a lumen positioned in the cam.

In some embodiments, the passageway comprises a lumen of approximately less than or equal to 5 mm in diameter.

In some embodiments, the passageway is constructed and arranged to receive a tool shaft up to approximately 5 mm in diameter.

In some embodiments, the passageway comprises a first passageway and a second passageway. The first passageway can comprise a first diameter, and the second passageway can comprise a second diameter different than the first diameter.

In some embodiments, the passageway comprises a non-circular cross section constructed and arranged to prevent rotation of the medical device shaft portion.

In some embodiments, the medical device comprises a tool guide constructed and arranged to slidingly receive the shaft of a second medical device. The tool guide can comprise a hollow tube. The tool guide can be constructed and arranged to receive the shaft of a tool selected from the group consisting of: a grasper; a claw; scissors; a cutter; a knife; an ablator; a cauterizer; a drug delivery apparatus; a radiation source; a laser emitter; an energy delivery element such as a RF electrode; a sensor such as a pressure sensor or a blood sensor; a camera; a magnet; a heating element; a cryogenic element; a retractor; a retractor blade such as a check retractor; and combinations thereof.

In some embodiments, the medical device comprises a medical device selected from the group consisting of: a grasper; a claw; scissors; a cutter; a knife; an ablator; a cauterizer; a drug delivery apparatus; a radiation source; a laser emitter; an energy delivery element such as a RF electrode; a sensor such as a pressure sensor or a blood sensor; a camera; a magnet; a heating element; a cryogenic element; a retractor; a retractor blade such as a check retractor; and combinations thereof.

In some embodiments, the medical device comprises a cheek retractor.

In some embodiments, the tool support further comprises a set screw. The set screw can be constructed and arranged to lock the cam to the support device elongate portion upon tightening of the set screw. As the set screw is tightened, the set screw can apply a force to the cam that causes the cam to frictionally engage the support device elongate portion. The set screw can be further constructed and arranged to lock the medical device to the passageway upon the tightening of the set screw. As the set screw is tightened, the set screw can apply a force to the cam that causes a portion of the cam to move into the passageway and frictionally engage the medical device shaft portion. The set screw can be constructed and arranged to lock the medical device to the passageway upon tightening of the set screw. As the set screw is tightened, the set screw can apply a force to the cam that causes a portion of the cam to move into the passageway and frictionally engage the medical device shaft portion. The set screw can be configured to prevent rotation of the cam relative to the outer shell upon tightening of the set screw.

In some embodiments, the tool support further comprises two set screws. A first set screw can be constructed and arranged to lock the cam to the support device elongate portion upon tightening of the first set screw and a second set screw can be constructed and arranged to lock the medical device to the passageway upon tightening of the second set screw.

In one aspect, provided is an oral retraction device as described herein, comprising: at least one tool support as described herein. The oral retraction device can be constructed and arranged to provide access to a location selected from the group consisting of: a nasal passage; throat; oropharynx; esophagus; vocal chords; stomach; and combinations thereof. The oral retraction device can comprise a closed perimeter frame. The oral retraction device comprises an open perimeter frame. The oral retraction device can further comprise a tooth engaging member constructed and arranged to stabilize the oral retraction device. The tooth engaging member can be constructed to contact at least one of the patient's teeth or gums. The tooth engaging member can comprise a rigid portion and a flexible portion.

In some embodiments, an oral retraction device comprises at least two, or at least three tool supports as described herein.

In one aspect, provided is an oral retraction system comprising: a tool support as described herein; and a controller for performing a movement function selected from the group consisting of: translating the passageway of the tool support along support device elongate portion; rotating the passageway of the tool support about the support device elongate portion; translate the medical device shaft portion within the passageway; lock the orientation of the passageway relative to the support device; lock the medical device shaft portion within the passageway; and combinations thereof.

In some embodiments, the oral retraction system further comprises at least one motor, wherein the controller is configured to operate the at least one motor to perform the movement function. The at least one motor can be fixed to the outer shell of the tool support and can be configured to rotate the outer shell relative to the cam. The at least one motor cam be fixed to the outer shell of the tool support and cam be configured to translate the medical device shaft portion relative to the passageway. The at least one motor can be fixed to the cam of the tool support and can be configured to translate the tool support relative to the support device.

In some embodiments, the oral retraction system further comprises at least one linear actuator, wherein the controller is configured to operate the at least one linear actuator to perform the movement function. The at least one linear actuator can comprise a solenoid. The at least one linear actuator can be fixed to the outer shell and can be configured to prevent rotation of the outer shell relative to the cam.

In one aspect, provided is an oral retraction system comprising: a tongue depressor assembly comprising: at least one a tongue depressor blade; a tube positioned along at least a portion of the at least one tongue depressor blade and comprising at least one opening; and a fluid attachment port in fluid communication with the at least one opening; wherein the tongue depressor assembly is configured to introduce and/or withdraw fluids through the at least one opening.

In some embodiments, the tube is constructed and arranged to attach to the at least one tongue depressor blade.

In some embodiments, the at least one tongue depressor blade comprises multiple tongue depressor blades.

In some embodiments, the oral retraction system further comprises a functional element. The functional element can be positioned on a component selected from the group consisting of: the at least one tongue depressor blade; the tube; the fluid attachment port; and combinations thereof. The functional element can comprise a sensor. The sensor can comprise a sensor selected from the group consisting of: a pressure sensor; a smoke sensor; a pH sensor; a blood gas sensor; blood glucose sensor; a respiration sensor; an EEG sensor; a temperature sensor; an electrode; and combinations thereof. The functional element can comprise a transducer. The transducer can comprise a transducer selected from the group consisting of: a light; an infrared light; a visible light; a radioactive element; an ultrasound delivery element; an electrode; a camera; and combinations thereof.

In another aspect, provided is a method for retracting a mouth of a patient during a medical procedure, comprising: coupling a tongue depressor blade to an oral retraction articulation assembly; inserting the tongue depressor blade into the mouth; moving the tongue depressor blade in a linear direction relative to the oral retraction articulation assembly; locking the tongue depressor blade at a desired linear position; moving the tongue depressor blade in an angular direction relative to the oral retraction articulation assembly; locking the tongue depressor blade at a desired angular position; removing the tongue depressor blade from the mouth; coupling the articulation assembly to a frame; positioning the frame about the mouth; reinserting the tongue depressor blade into the mouth; and moving the tongue depressor blade in a rotational direction relative to the oral retraction articulation assembly.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same elements throughout the different views. The drawings are not necessarily to scale, emphasis instead being placed upon illustrating the principles of the preferred embodiments.

FIG. 2 is a close-up cutaway side view of a linear positioning assembly of an oral retractor in a first position, in accordance with embodiments of the present inventive concepts.

FIG. 2A is a close-up cutaway side view of the linear positioning assembly of FIG. 2, in a second position.

FIG. 2B is a close-up top view of the linear positioning assembly of FIGS. 2 and 2A, illustrating a rotational adjustment of a tongue depressor blade, in accordance with embodiments of the present inventive concepts.

FIG. 3 is a view of various tongue depressor blades, in accordance with embodiments of the present inventive concepts.

FIG. 5 is a view of a system including a robotically manipulatable oral retractor, in accordance with embodiments of the present inventive concepts.

FIGS. 5A-5C are side sectional views of a portion of an oral retractor of FIGS. 1-5, in accordance with embodiments of the present inventive concepts.

FIG. 9 is a view of a system including a robotically manipulatable tool holder, in accordance with embodiments of the present inventive concepts.

DETAILED DESCRIPTION OF EMBODIMENTS

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Figure 1A:
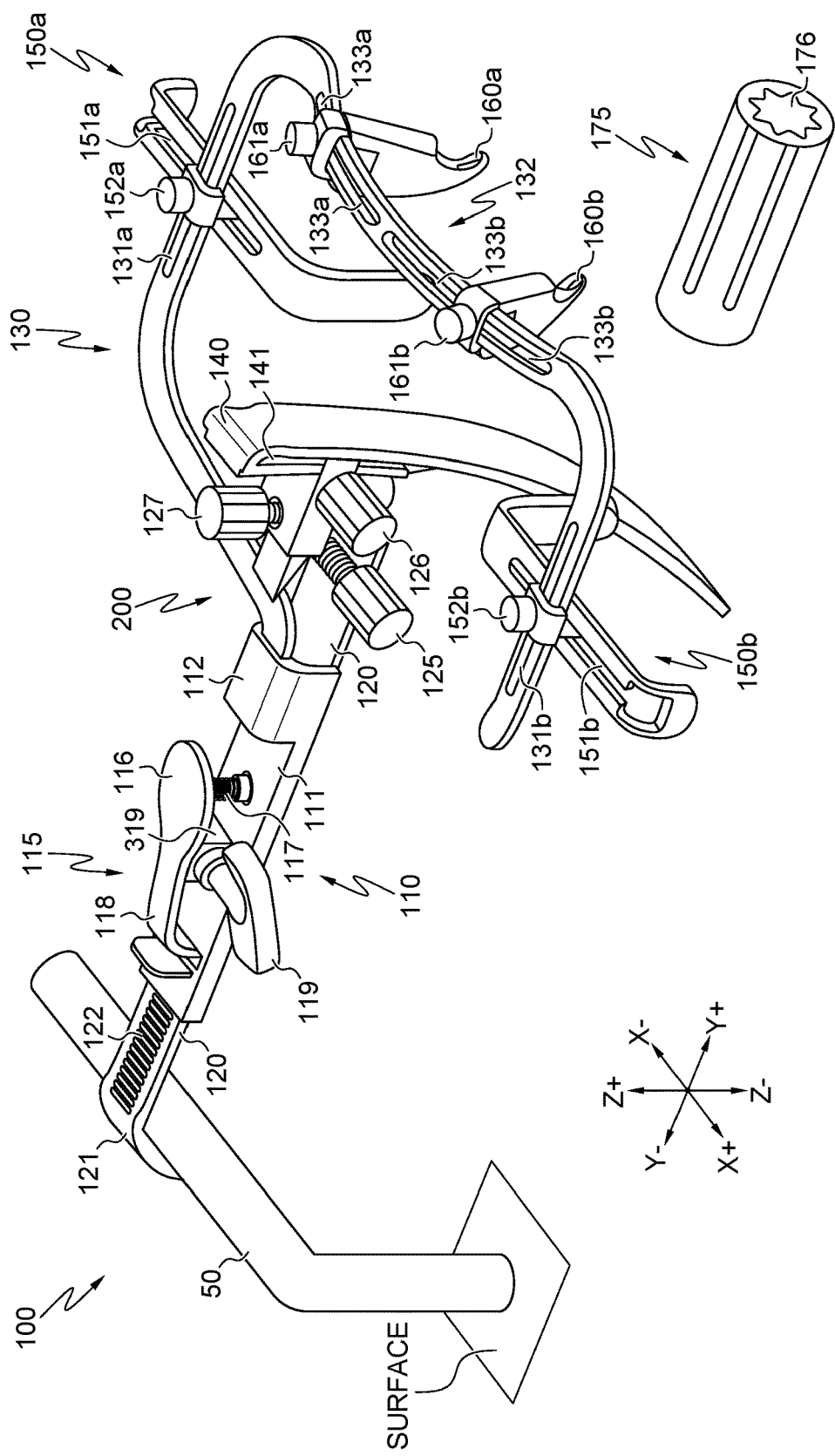
FIG. 1A is an isometric view of an oral retractor, in accordance with embodiments of the present inventive concepts.
Figure 1B:
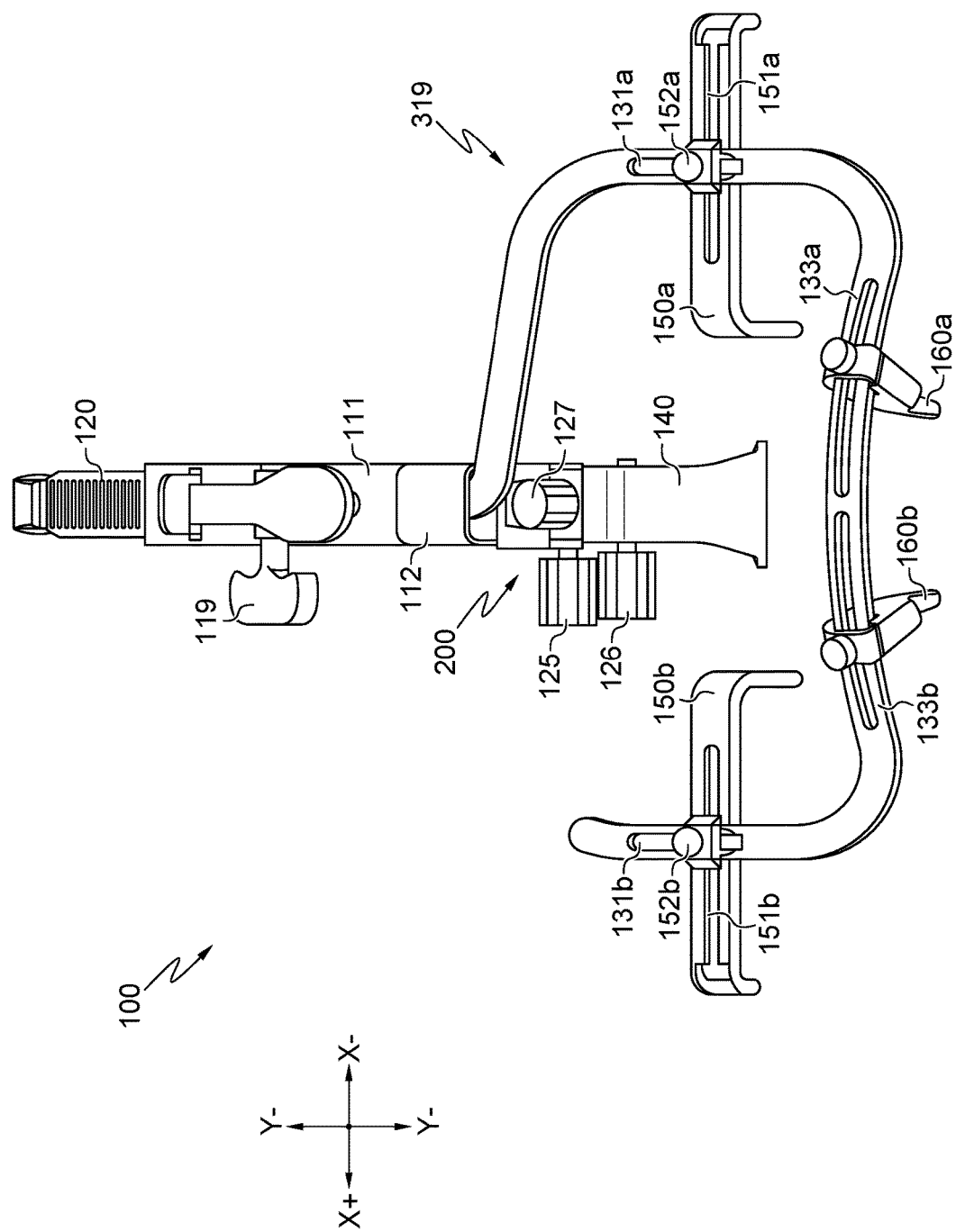
FIG. 1B is a top view of the oral retractor of FIG. 1A, in accordance with embodiments of the present inventive concepts.
Figure 1C:
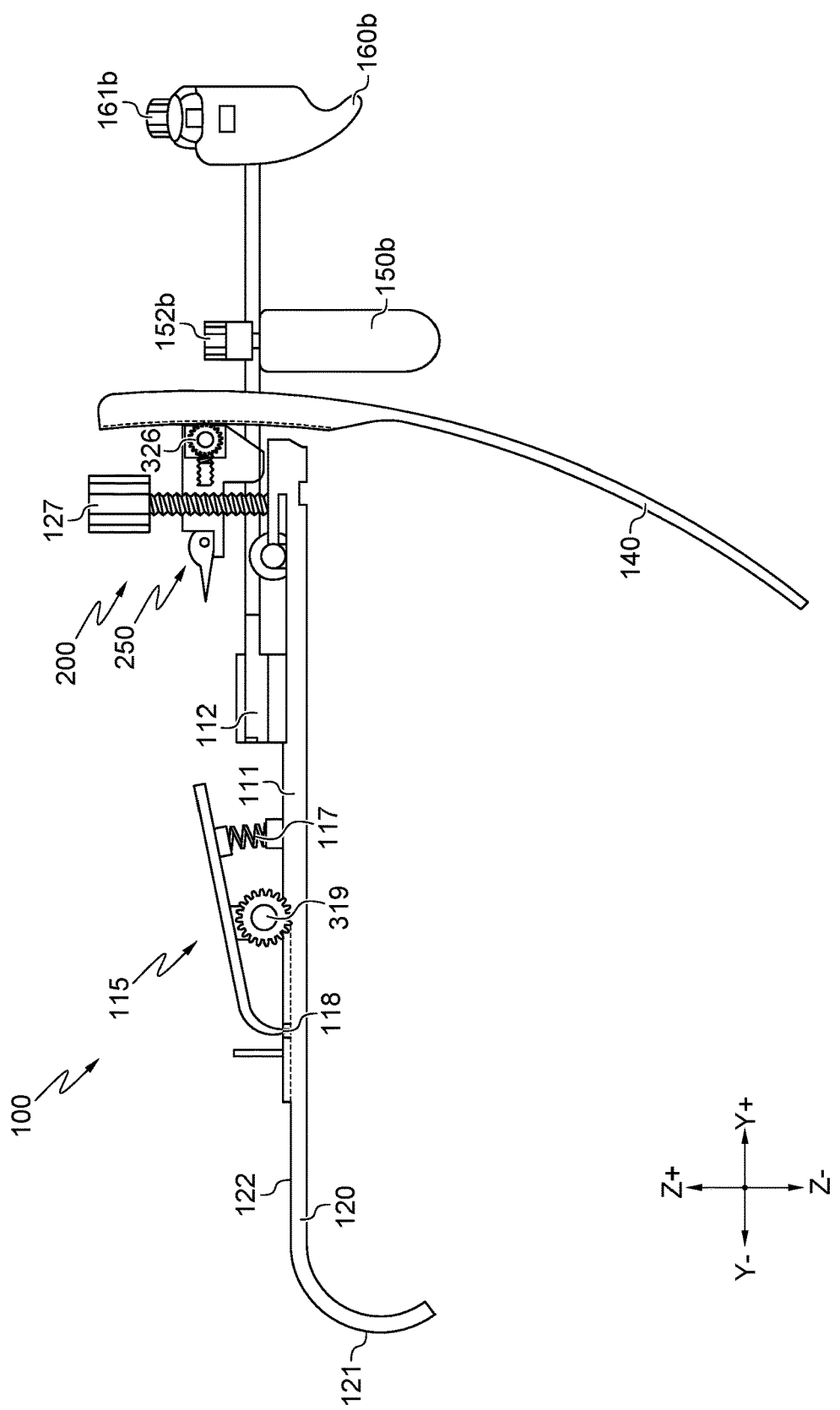
FIG. 1C is a cutaway side view of the oral retractor of FIGS. 1A and 1B, in accordance with embodiments of the present inventive concepts.

FIG. 1A is an isometric view of an oral retractor 100, in accordance with embodiments of the present inventive concepts. FIG. 1B is a top view of the oral retractor 100 of FIG. 1A, in accordance with embodiments of the present inventive concepts. FIG. 1C is a cutaway side view of the oral retractor 100 of FIGS. 1A and 1B, in accordance with embodiments of the present inventive concepts. The oral retractor 100 is positioned along X, Y, and Z axes, also referred to as frontal, longitudinal, and sagittal axes, respectively. As used herein, the X+ axis refers to an axis that can extend towards a patient's left side, the X− axis refers to an axis that can extend towards the patient's right side, the Y+ axis refers to an axis that can extend toward the patient's head, the Y− axis refers to an axis that can extend toward the patient's feet, the Z+ axis refers to an axis that can extend above the patient, and the Z-axis refers to an axis that can extend below the patient.

The oral retractor 100 is constructed and arranged to maintain an opening at a patient's mouth and to retract at least a portion of the patient's mouth during a medical procedure. The retractor 100 can be constructed and arranged to provide access (i.e. through the mouth) to a nasal passage, throat or related oral cavity, oropharynx, larynx, esophagus, vocal chords, stomach, and/or to directly or indirectly access regions of the body proximal to the nasal passage, throat, oropharynx, larynx, esophagus, vocal chords, and/or stomach. The retractor 100 can be used to introduce an articulating robotic probe and/or related surgical tools, such as the probe described in the PCT application, published under WO 2012/167043 on Jan. 24, 2013, the contents of which is incorporated herein by reference in its entirety. A surgical tool may include but not be limited to a claw, scissors, a cutter, a knife, an ablator, a cauterizer, a drug delivery apparatus, a radiation source, a laser emitter, an energy delivery element such as a RF electrode, a light source, a sensor such as a pressure sensor or a blood sensor, a camera, a magnet, a heating element, a cryogenic element, or a combination thereof.

The oral retractor 100 exposes areas of a human anatomy by allowing an operator, for example, a head and neck surgeon or other medical professional, to apply forces via the retractor 100 to the lips, tongue, teeth, and/or cheeks to control the geometry of the patient's mouth, for example, a size of the mouth opening. The retractor 100 is preferably in a stabilized state when applying the forces. A feature of the retractor 100 in accordance with embodiments of the present inventive concepts is that an operator, e.g., a surgeon, can gain simple and/or rapid access and exposure (via the patient's mouth) to the oropharynx, larynx, hypopharynx, or other internal regions of a body due to the ease of insertion and significant operator adjustability of multiple retraction elements of oral retractor 100, as well the low profile configuration of oral retractor 100 and availability of different tongue suppressor blade shapes, for example, shown in FIG. 3. Articulation of one or more positionable components of oral retractor 100 can provide better visualization and/or access to deeper or otherwise hard-to-reach anatomical locations than would be available without the enhanced articulation.

In an embodiment, the oral retractor 100 includes an articulation assembly 200 and a support element including a support arm 120. The articulation assembly 200 includes a linear positioning assembly 110 and a main support frame 130. Main support frame 130 is attached to positioning assembly 110, and positioning assembly 110 is operatively attached to support arm 120 such that operation of positioning assembly 110 causes the linear translation of main support frame 130 relative to support arm 120. Oral retractor 100 further includes a tongue depressor blade 140 which is operably attached to support arm 120 via tongue depressor articulation assembly 200. Oral retractor 100 can comprise at least one cheek retractor 150a, 150b (generally, 150).

Support arm 120 comprises a first support element, or attachment portion 121, which can be configured to provide a stabilizing force to oral retractor 100 as described in detail herein. Main support frame 130 can be configured as a second support element of oral retractor 100, such as to provide a supporting force proximate both ends of retractor 100. As described herein, the tongue depressor blade 140, the check retractors 150 and/or one or more other components of oral retractor 100 can be disposable, e.g. disposed of after a single a limited number of clinical procedures. In some embodiments, one or more tongue depressor blades 140 and/or other component of oral retractor 100 can comprise a non-conductive material such as a non-conductive plastic or a metal with a non-conductive coating.

Figure 4:
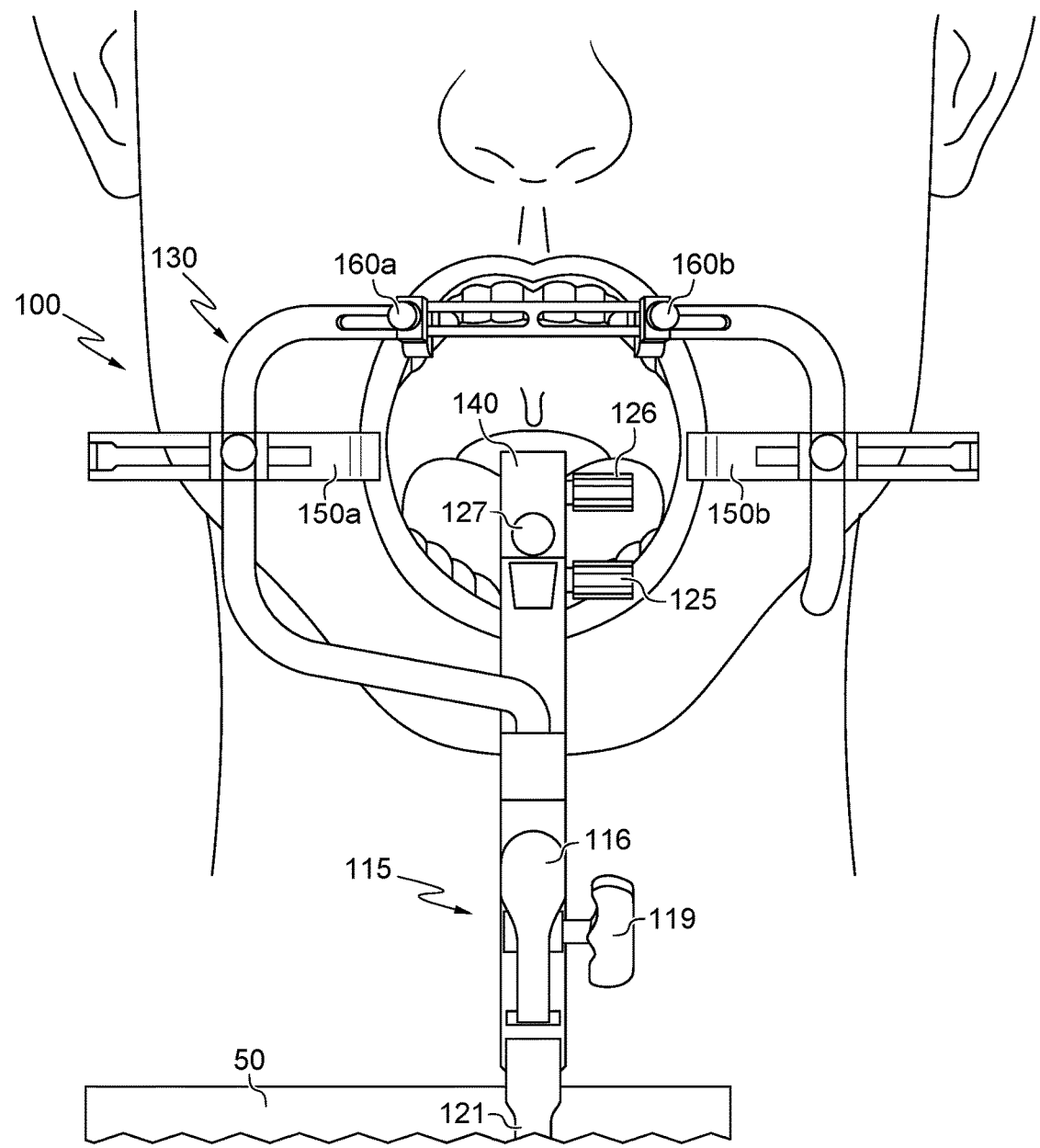
FIG. 4 is a view of an oral retractor positioned in a patient's mouth, in accordance with embodiments of the present inventive concepts.

The linear positioning assembly 110 comprises a base 111, a ratchet assembly 115, and one or more gears 319. The main support frame 130 is coupled to an attachment point 112 at a distal end of the base 111 of the linear positioning assembly 110. The main support frame 130 can be formed of stainless steel, plastic, or other well-known material that provides structural rigidity for positioning a patient's head and mouth and maintaining the mouth in an open position, as shown in FIG. 4. Components for retracting portions of the mouth region such as the cheek retractors 150 can be coupled to the main support frame 130. Other components such as one or more molar supports 160, a mouth guard, and the like, can be coupled to the main support frame 130. The molar supports 160 are adjustable with respect to their position on the main support frame 130 to accommodate a location of a patient's molar teeth, for example, an asymmetrical location of molar teeth.

The main support frame 130 can include two or more cheek positioning slots 131a, 131b (generally, 131), a molar adjustment arch 132, and two or more molar adjustment slots 133a, 133b (generally, 133). The main support frame 130 can be configured to include multiple sections extending along different directions about its periphery. For example, the cheek positioning slots 131 and the molar adjustment slots 133 can be at different sections of the support frame 130, and as shown in FIG. 1A. Here, the cheek positioning slots 131 can be constructed and arranged for positioning the cheek retractors 150 along the main support frame 130 along the Y axis, and the molar adjustment slots 133 can extend in a direction along the X axis.

One or more removable molar supports 160a, 160b (generally 160) can be coupled to the main support frame 130 at the molar adjustment arch 132. The molar adjustment slots 133 can extend through a portion of the main support frame 130 at the molar adjustment arch 132. The molar adjustment arch 132 is configured so that the molar supports 160 can be aligned with a patient's molar teeth, or other teeth or portion of the upper jaw of the patient, or adaptive connector.

Linear positioning assembly 110 is constructed and arranged to allow operator translation of main support frame 130 along the Y axis (e.g. to change the distance between molar supports 160 and tongue depressor blade 140). Support arm 120 comprises multiple engageable ridges, teeth 122 on its top surface as shown. Positioning assembly 110 includes gear 319 which operatively engages teeth 122. Gear 319 is attached to linear positioning knob 119 such that rotation of linear positioning knob 119 causes rotation of gear 319 about its axis and subsequent linear translation of positioning assembly 110 with respect to support arm 120. In some embodiments, positioning assembly 110 is configured to limit translation in one or more directions. For example, positioning assembly 110 can include ratchet assembly 115 comprising lever 116 with locking portion 118, and spring assembly 117. Ratchet assembly 115 is biased by spring assembly 117 such that locking portion 118 is engaged with teeth 122. Lever 116 and locking portion 118 are constructed and arranged to allow translation of positioning assembly 110 along the Y+ axis (e.g. in a ratcheting fashion), while preventing motion along the Y− axis. When a force is applied to the proximal end of the lever 116, for example, by an operator applying pressure along the Z− axis, the locking portion 118 is released, or disengaged from the teeth 122, permitting the positioning assembly 110 to freely move along both directions of the Y axis. In some embodiments, positioning assembly 110 is configured to translate by manually applying opposing forces to positioning assembly 110 and support arm 120, without manual rotation of linear positioning knob 119, i.e. sufficient force to cause rotation of gear 319 along teeth 122.

Attachment portion 121 of support arm 120 can be configured to attach to a support rod or other support structure 50. Attachment portion 121 can comprise a partial circumferential shape configured to partially surround a tubular portion of support structure 50 (as shown in FIG. 1A) or otherwise engage support structure 50 to stabilize and/or maintain the position of support arm 120. Alternatively, attachment portion 121 can be configured as a handle for stabilization by an operator of oral retractor 100.

Support arm 120 can be attached to a tongue depressor blade 140, also referred to as a tongue depressor, via the articulation assembly 200. The tongue depressor blade 140 is removably coupled to the articulation assembly 200. The tongue depressor blade 140 can be disposable, such as a tongue depressor blade 140 that is constructed and arranged to be used in one or more medical procedures. The other elements of the retractor 100, including at least the linear positioning assembly 110, the support arm 120, the main support frame 130, and/or the articulation assembly 200 can be constructed and arranged to be used in one or more medical procedures, such as to be used in more medical procedures than the tongue depressor blade 140, especially since different tongue depressor blades 140, for example, various tongue depressor blades shown in FIG. 3, can be removably attached to the retractor 100. For example, the retractor 100 configured with a particular tongue depressor blade 140 shown in FIG. 3 can be used in one or more medical procedures on one patient. The blade 140 can be removed from the retractor 100, and replaced with a different blade 140 shown in FIG. 3 that is used in one or more medical procedures, for example, inserted into the mouth of a different patient. The tongue depressor blades in FIG. 3 can be disposable, and each is configured for a particular shape or function, thereby enhancing exposure to the oral cavity of each patient receiving the oral retractor 100.

The articulation assembly 200 includes a multi-axis gear assembly controlled by a rotational positioning knob 125, a height positioning knob 126, and an angular positioning knob 127 for articulating the tongue depressor blade 140 in accordance with one or more degrees of freedom. The tongue depressor blade 140 can be pivoted about the X axis using the angular positioning knob 127, the insertion length of the blade 140 can be adjusted using the height positioning knob 126, and/or the blade 140 can be rotated about the Z axis using the rotational positioning knob 125. A rotation of the rotational positioning knob 125 drives an articulation of the tongue depressor blade 140 in a curvilinear direction with a single degree of freedom about the Z axis, for example, shown in FIG. 2B. The frame 130 is preferably coupled to the articulation assembly 200 and positioned about the patient's mouth for stability when determining a desirable rotational position of the blade 140.

A rotation of the height positioning knob 126 drives an articulation of the tongue depressor blade 140 relative to the articulation assembly 200 in a linear direction with a single degree of freedom along the Z axis. Accordingly, tongue depressor blade 140 can be inserted in a patient's mouth, whereby a user can move the tongue depressor blade 140 up and down in the mouth to determine a linear position of the blade 140 prior to coupling the frame 130 to the articulation assembly 200. A rotation of the angular positioning knob 127 drives an articulation of the tongue depressor blade 140 in a curvilinear direction, or pitch, with a single degree of freedom about the X axis. Accordingly, tongue depressor blade 140 can be inserted in a patient's mouth, whereby a user can move the tongue depressor blade 140 up and down in the mouth to determine a desirable angular position or pitch of the blade 140 prior to coupling the frame 130 to the articulation assembly 200. Engagement of a combination of one or more of the rotational positioning knob 125, height positioning knob 126, and the angular positioning knob 127 can permit articulation of the tongue depressor blade 140 to occur with one, two, and/or three degrees of freedom and therefore enable enhanced patient access through the mouth during a medical procedure (e.g. without significant neck extension and/or without the need for a strong reclination of the patient's head). Additional modification of exposure geometry (e.g. additional degrees of freedom) can be achieved through rotation of linear positioning knob 119 which causes translation of main support frame 130 including molar supports 160 and cheek retractors 150, described herebelow.

For example, during an operation including the oral retractor 100, the blade 140 is coupled to the articulation assembly 200, and introduced to the oral cavity. The operator can move the blade 140 up and down along the Z axis relative to the articulation assembly 200 until a desired linear position is determined by rotating the height positioning knob 126. The operator can lock the linear position of the blade 140 in place, then determine a desired pitch of the blade 140 by rotating the angular positioning knob 127. After the desired linear and angular position of the blade 140 are determined, and the blade 140 is locked in place relative to the assembly 200, the blade 140 can be removed from the oral cavity and coupled to the frame 130. The frame 130 can be positioned on the patient's face, and about the patient's oral cavity for stabilizing the blade 140. The blade 140 is reinserted into the oral cavity at the previously determined height and angular position. The operator can rotate the blade 140 axially, i.e., about the Z axis, by rotating the rotational positioning knob 125.

The retractor 100 can include two or more cheek retractors 150*a*, 150*b* (generally, 150). Cheek retractor 150*a* can include a groove 151*a* and a clamp 152*a*. Cheek retractor 150*b* can include a groove 151*b* and a clamp 152*b*. The clamps 152*a*, 152*b* (generally, 152) can be configured to attach the cheek retractors 150 to the main support frame 130 via the grooves 151*a*, 151*b*, respectively (generally, 151). Clamps 152 are configured to be tightened to maintain a set position of the cheek retractors 150 relative to the main support frame 130, or can be loosened to permit the cheek retractors 150 to freely move relative to the main support frame 130. In particular, the clamps 152 can each include a knob, screw, and/or other coupling mechanism permitting a corresponding cheek retractor 150 to translate linearly along the Y axis with respect to a cheek positioning slot 131 in the main support frame 130. The clamps 152 can each extend through a corresponding groove 151 for coupling to the main support frame 130. The grooves 151 can extend along the X axis. Thus, a cheek retractor 150 can also, or alternatively, translate linearly along the X axis by sliding the groove 151 of the cheek retractor 150 relative to a clamp 152 positioned in the groove 151. The cheek retractors 150 can also, or alternatively, rotate about an axis parallel to the Z axis at clamps 152.

As described herein, the cheek retractors 150 can be removably coupled to the main support frame 130 and can be disposable. The cheek retractors 150 are constructed and arranged to be used in one or more medical procedures. The other elements of the retractor 100, including at least the linear positioning assembly 110, the support arm 120, the main support frame 130, and the articulation assembly 200 are constructed and arranged to be used in one or more medical procedures, such as to be used in less, the same or more medical procedures than the cheek retractors 150. For example, the retractor 100 configured with a particular set of cheek retractors 150 can be used in one or more medical procedures on one patient. The cheek retractors 150 can be removed from the retractor 100, and replaced with cheek retractors 150 that are used in one or more medical procedures on a different patient. In this example, the other elements of the retractor 100 such as the positioning assembly 110, etc. are used in both patient procedures, i.e., procedures including the use of both sets of cheek retractors 150.

As previously described, the retractor 100 can include two or more molar supports 160a, 160b (generally, 160) configured to be positioned in molar adjustment slots 133 of the main support frame 130 at an arch 132 extending along the X axis, for aligning with the molar teeth of a patient, or other teeth or portion of the upper jaw of the patient. Molar support 160a can include a clamp 161a. Molar support 160b can include a clamp 161b. The clamps 161 are each configured to movably couple a corresponding molar support 160 to the main support frame 130 via a molar adjustment slot 133 in the main support frame 130 so that the molar support 160 can translate linearly along the X axis. The clamps 161 can each include a knob, screw, and/or other coupling mechanism configured to be tightened to maintain a set position of the molar support 160 relative to the main support frame 130, or can be loosened to permit the molar support 160 to freely move relative to the main support frame 130.

The molar supports 160 can therefore provide a resistive force for the main support frame 130 such that the translation of the support arm 120 along the Y+ axis can spread open the patient's mouth along the Y axis, for example, shown in FIG. 4. Cheek retractors 150 can therefore provide a resistive force to spread the patient's mouth open along the X axis.

Additional modification of exposure geometry can be achieved by adjusting the position of one or more molar supports 160 (e.g. using clamp 161) and/or one or more cheek retractors 150 (e.g. using clamp 152).

In some embodiments, oral retractor 100 further comprises one or more tools 175 including engagement portion 176. Engagement portion 176 comprises a geometry configured to frictionally engage one or more of: rotational positioning knob 125, height positioning knob 126, angular positioning knob 127 or linear positioning knob 119. Tool 175 is constructed and arranged to be gripped by one or more fingers of an operator's single hand and to provide a mechanical advantage in turning the engaged component. Therefore, tool 175 can be provided as an extension that when coupled to the knob 125, 126, 127, 119 permits a user to rotate the knob 125, 126, 127, 119 from a location other than the articulating assembly 200, for example, outside the perimeter of the frame 130.

Articulation or other geometric modification of one or more portions of oral retractor 100 can comprise a one-handed operation. For example, while engaged with a patient's mouth and stabilized by support structure 50 via attachment portion 121 (as shown in FIG. 4 herebelow), one or more adjustment elements can be operated with a single hand of an operator. Single handed adjustment of tongue depressor blade 140 can be achieved by turning rotational positioning knob 125, height positioning knob 126 and/or angular positioning knob 127. Single handed adjustment of main support frame 130 can be achieved by turning linear positioning knob 119 and/or depressing lever 116. Single handed adjustment of a cheek retractor 150 can be achieved by loosening the associated clamp 152, repositioning cheek retractor 150 and re-tightening the clamp 152. Single handed adjustment of a molar support 160 can be achieved (e.g. when not in contact with the patient's teeth) by loosening the associated clamp 161, repositioning molar support 160, and re-tightening the clamp 161.

FIG. 2 is a close-up cutaway side view of an articulation assembly 200 of an oral retractor in a first position, in accordance with embodiments of the present inventive concepts. FIG. 2A is a close-up cutaway side view of the articulation assembly 200 of FIG. 2 in a second position.

FIG. 2B is a close-up view of the positioning assembly of FIGS. 2 and 2A, illustrating a rotational adjustment of the tongue depressor blade 140, in accordance with embodiments of the present inventive concepts. The articulation assembly 200 can be constructed and arranged as part of the oral retractor 100 described with reference to FIGS. 1A-1C. Thus, a description of elements of the oral retractor 100 is not repeated due to brevity. The articulation assembly 200 is positioning along the X, Y, and/or Z axes referred to in FIGS. 1A-1C.

The articulation assembly 200 comprises a first portion 201 and a second portion 202 in communication with the first portion 201. The first portion 201 is also coupled to the support arm 120 via an axle 205 extending along the Z axis.

As shown in FIG. 2B, the rotational positioning knob 125 comprises a gear 325 which rotatably engages a gear 301 coupled to a proximal end of the first portion 201. A rotation of the positioning knob 125 drives an articulation of the first portion 201 about the axle 205 extending along the Z axis.

The second portion 202 of the articulation assembly 200 is configured to rotate relative to the first portion 201 about an axle 210 extending along the X axis (extending in and out of the sheet). The angular positioning knob 127 is configured to act as a stop lock when the second portion 202 rotates about the axle 210, for example, shown at FIG. 2A. The second portion 202 comprises one or more arms 203 configured to abut and slidingly receive a tongue depressor blade 140 via a channel 141. The tongue depressor blade 140 comprises a set of geared teeth 142 configured to frictionally engage a gear 326 of the multi-axis gear assembly coupled to an axle that extends along the X axis. The gear 326 can be coupled to the height positioning knob 126, and can rotate about its axle in response to a rotation of the height positioning knob 126. In doing so, the rotation of the gear 326 engages the geared teeth 142, which in turn moves the tongue depressor blade 140 via the channel 141 along a linear path thereby adjusting a vertical position of the tongue depressor blade 140 relative to the arms 203 of the second portion 202 of the articulation assembly 200.

Articulation assembly 200 comprises a locking assembly 250, including lever 251, axle 252, pin 253, and spring 254. Locking assembly 250 is constructed and arranged to, when in the locked position as shown in FIG. 2A, frictionally engage pin 253 with gear 326, locking the horizontal position of tongue depressor 140. In an unlocked position, as shown in FIG. 2, lever 251 is rotated (clockwise as shown) about axle 252, allowing spring 254 to pull pin 253 away from and disengaging gear 326. In the unlocked position, gear 326 is free to rotate such as to adjust the depth position of tongue depressor 140, for example, when inserted into the oral cavity at a medical procedure. In some embodiments, lever 251 can be configured to be a quick release mechanism such as a mechanism released via a single finger or single hand of an operator.

In some embodiments, tongue depressor blade 140 is constructed and arranged to be removed while oral retractor 100 is positioned in the patient's mouth. Tongue depressor blade 140 can be removed by sufficient rotation of height positioning knob 126 to cause tongue depressor blade 140 to translate vertically until geared teeth 142 disengage from gear 326. Alternatively or additionally, gear 326, geared teeth 142 and/or articulation assembly 200 can be constructed and arranged such that an operator can grip tongue depressor blade 140 (e.g. with a single hand), and apply a force sufficient to cause rotation of gear 326 and eventual disengagement of geared teeth 142 with gear 326, that is, with or without directly manipulating gear 326.

FIG. 4 is a view of an oral retractor positioned in a patient's mouth, in accordance with embodiments of the present inventive concepts. Oral retractor 100 is positioned in a patient's mouth to provide access to an internal location of the patient during one or more medical procedures as described hereabove. Oral retractor 100 is supported on one end by a first support element, attachment portion 121 engaged with support rod 50, and on its other end by a second support element, main support frame 130 engaged with the patient's mouth. Support rod 50 can be attached to one or more stable structures such as a patient table or the floor. Exposure for a medical procedure is accomplished by application of a force on the patient's tongue by tongue depressor blade 140, application of one or more forces on the patient's cheeks by one or more cheek retractors 150 and/or application of one or more forces on the patient's teeth by one or more molar supports 160, as shown.

Oral retractor 100 can include linear positioning knob 119 which can be rotated by an operator to adjust the force applied to the patient's teeth (e.g. to adjust the opening through the mouth) by changing the distance between main support frame 130 relative to tongue depressor blade 140, as described hereabove. Oral retractor 100 can include ratchet assembly 115 which can be configured to allow operator selectable translation in a single direction or both directions along the Y axis, as described hereabove. In some embodiments, ratchet assembly 115 is configured to allow rapid release of force applied to the patient's molars (e.g. by pressing lever 116), such as to allow rapid removal of oral retractor 100 from the patient's mouth.

Oral retractor 100 can be constructed and arranged to allow geometric adjustment and/or adjustment of applied forces to the patient with single-handed operations, such as is described hereabove in reference to FIG. 1.

FIG. 5 is a view of a system including a robotically manipulatable oral retractor, in accordance with embodiments of the present inventive concepts. System 10 comprises human interface device (HID) 11, controller 12 and retractor 100. Retractor 100 can be constructed and arranged as described in reference to FIGS. 1-5 hereabove. Controller 12 comprises one or more wires or other power and/or signal carrying conduits, wire bundle 332 which are operably attached to retractor 100. HID 11 comprises a user interface that allows an operator to send commands to control one or more portions of oral retractor 100 via power and/or information by controller 12 via wire bundle 332. System 10 can be configured to allow an operator to interface with HID 11 to adjust or otherwise control retractor 100, such as to operate one or more controls of retractor 100, such as linear positioning knob 119, rotational positioning knob 125, height positioning knob 126 and/or angular positioning knob 127 of oral retractor 100 of FIGS. 1-5 described hereabove. Oral retractor 100 can comprise one or more motors or other drive elements configured to respond to the power and/or information delivered by controller 12, such as is described in reference to FIGS. 5A-5C herebelow, such as to rotate or otherwise adjust one or more controls of oral retractor 100.

System 10 can include an articulating probe apparatus, such as an apparatus including probe feeder 13 and articulating probe 14. System 10 can further include one or more tools, such as tools 15a and/or 15b. Tool 15a is shown inserted through feeder 13 and exiting the distal end of probe 14. Tool 15b is shown passing through a side channel of a distal portion of probe 14. In some embodiments, HID 11, controller 12, probe feeder 13 and/or articulating probe 14 are constructed and arranged as described in the PCT application, published under WO 2012/167043 on Jan. 24, 2013, and/or U.S. Provisional application Ser. No. 61/751, 498, filed Jan. 11, 2013, the contents of each of which is incorporated herein by reference in its entirety.

FIG. 5A is a side sectional view of a portion of a particular embodiment of the oral retractor 100 of FIGS. 1-5, in accordance with embodiments of the present inventive concepts. A motor or other rotational drive assembly, motor 330a, is attached to support arm 120 via one or more welds 331. Motor 330a is connected to a portion of wire bundle 332 of FIG. 5, wire 332a. Motor 330a is connected to gear 325, such that rotation of gear 325 by motor 330 drives an articulation of the tongue depressor blade 140 in a curvilinear direction with a single degree of freedom about the Z axis, for example, shown in FIG. 2B.

FIG. 5B is a side sectional view of a portion of another particular embodiment of the oral retractor 100 of FIGS. 1-5, in accordance with embodiments of the present inventive concepts. A motor or other rotational drive assembly, motor 330b or 330c, is attached to second portion 202 of articulation assembly 200 or base 111 of linear positioning assembly 110, respectively, via one or more welds 331. Motor 330b,c is connected to a portion of wire bundle 332 of FIG. 5, wire 332b or 332c respectively. Motor 330b, c is connected to gear 319 or 326, respectively. Rotation of gear 319 by motor 330b drives a linear translation of positioning assembly 110 along the Y axis. Rotation of gear 326 by motor 330c drives an articulation of the tongue depressor blade 140 in a linear direction with a single degree of freedom along the Y axis.

FIG. 5C is a side sectional view of a portion of a particular embodiment of the oral retractor 100 of FIGS. 1-5, in accordance with embodiments of the present inventive concepts. A motor or other rotational drive assembly, motor 330d, is attached to second portion 202 via one or more welds 331. Motor 330d is connected to a portion of wire bundle 332 of FIG. 5, wire 332d. Motor 330d is connected to a particular configuration of angular positioning knob 127 comprising gear 327a and mating threaded rod 327b. Rotation of gear 327a by motor 330d drives an articulation of the tongue depressor blade 140 in a curvilinear direction with a single degree of freedom about the X axis.

One or more of motors 330a-d can be configured to receive commands from controller 12 via wire bundle 332 to allow an operator to adjust the configuration of oral retractor 100.

Figure 6:
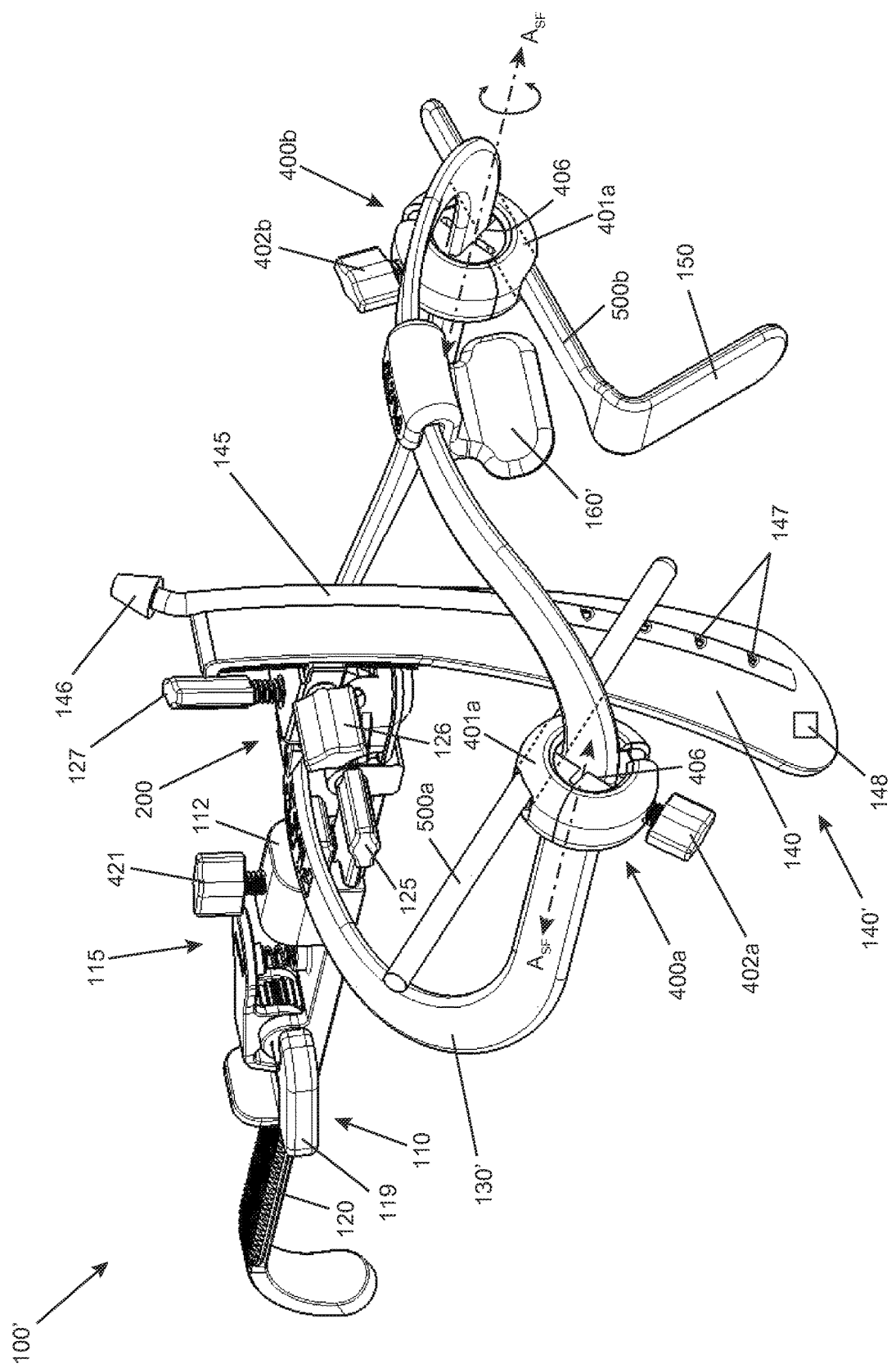
FIG. 6 is an isometric view of an oral retractor, in accordance with embodiments of the present inventive concepts.

FIG. 6 is an isometric view of an oral retractor 100', in accordance with embodiments of the present inventive concepts. Oral retractor 100' can be constructed and arranged similar to oral retractor 100 described hereabove in reference to FIG. 1. For example, oral retractor 100' can include linear positioning assembly 110, ratchet assembly 115, support arm 120, articulation assembly 200, each of which can be of similar construction and arrangement to the similar components of oral retractor 100 of FIG. 1. Oral retractor 100' is constructed and arranged to maintain an opening at a patient's mouth and to retract at least a portion of the patient's mouth during a medical procedure. Oral retractor 100' can be constructed and arranged to provide direct (i.e. through the mouth) and/or indirect access to a location selected from the group consisting of: a nasal passage; throat; oropharynx; esophagus; vocal chords; stomach; and combinations of these. Oral retractor 100' can be used to introduce and/or support an articulating robotic probe and/or other surgical tools, such as the probe described in the PCT application, published under WO 2012/167043 on Jan. 24, 2013, the contents of which is incorporated herein by reference in its entirety. Applicable surgical tools can include one or more tools selected from the group consisting of: a grasper; a claw; scissors; a cutter; a knife; an ablator; a cauterizer; a drug delivery apparatus; a radiation source; a laser emitter; an energy delivery element such as a RF electrode; a sensor such as a pressure sensor or a blood sensor; a camera; a magnet; a heating element; a light source, a cryogenic element; a retractor; a retractor blade such as check retractor 150; and combinations of these.

Oral retractor 100' includes main support frame 130', which can comprise a closed (as shown) or open perimeter frame. Main support frame 130' and/or one or more components of tool holder 400 can be constructed of one or more rigid materials, such as a metal such as stainless steel or titanium or a rigid plastic. Main support frame 130' is attached to positioning assembly 110, and positioning assembly 110 can be operatively attached to support atm 120 such that operation of positioning assembly 110 causes the linear translation of main support frame 130' relative to support arm 120, such as has been described hereabove. Main support frame 130' can comprise a thickness of approximately 0.125" and can comprise a width of approximately 0.5". In the embodiment of FIG. 6, main support frame 130' is removably attached to positioning assembly 110 via a tightened securing knob 421. Loosening of securing knob 421 allows main support frame 130' to be slidably removed from positioning assembly 110.

Oral retractor 100' can comprise one or more tool holders, such as tool holders 400a and 400b shown attached to main support frame 130' in FIG. 6. Tool holders 400a and/or 400b can be slidingly attached (e.g. pre-attached or operator attachable and/or removable) to main support frame 130'. In some embodiments, tool holder 400 can be laterally attached to main support frame 130' as is described herebelow in reference to FIG. 8. Tool holder 400a and tool holder 400b (singly or collectively tool holder 400) each comprise slot 406 which surrounds an elongate portion of main support frame 130'. Tool holder 400a and tool holder 400b each comprise a passageway 401a and 401b, respectively (singly or collectively passageway 401), which is configured to slidingly receive a shaft portion (e.g. shaft portions 500a or 500b described herebelow) of a cheek retractor, a tool guide (e.g. a hollow tube constructed and arrange to slidingly receive the shaft of a tool) or other medical device comprising a shaft portion. Passageway 401 and/or a shaft portion 500 comprises a tool guide and can be constructed and arranged to receive one or more tools selected from the group consisting of: grasper; a claw; scissors; a cutter; a knife; an ablator; a cauterizer; a drug delivery apparatus; a radiation source; a laser emitter; an energy delivery element such as a RF electrode; a sensor such as a pressure sensor or a blood sensor; a camera; a magnet; a heating element; a cryogenic element; a retractor; a retractor blade such as check retractor 150; and combinations of these. In some embodiments, passageway 401 comprises a diameter up to approximately 5 mm, such as to slidingly receive a shaft with a major diameter of approximately 5 mm or less. Passageway 401 can comprise a hole or other passageway contained within tool holder 400. Passageway 401 can comprise a circular or non-circular cross section, such as a non-circular cross section constructed and arranged to prevent rotation of an inserted shaft portion 500.

Figure 7:
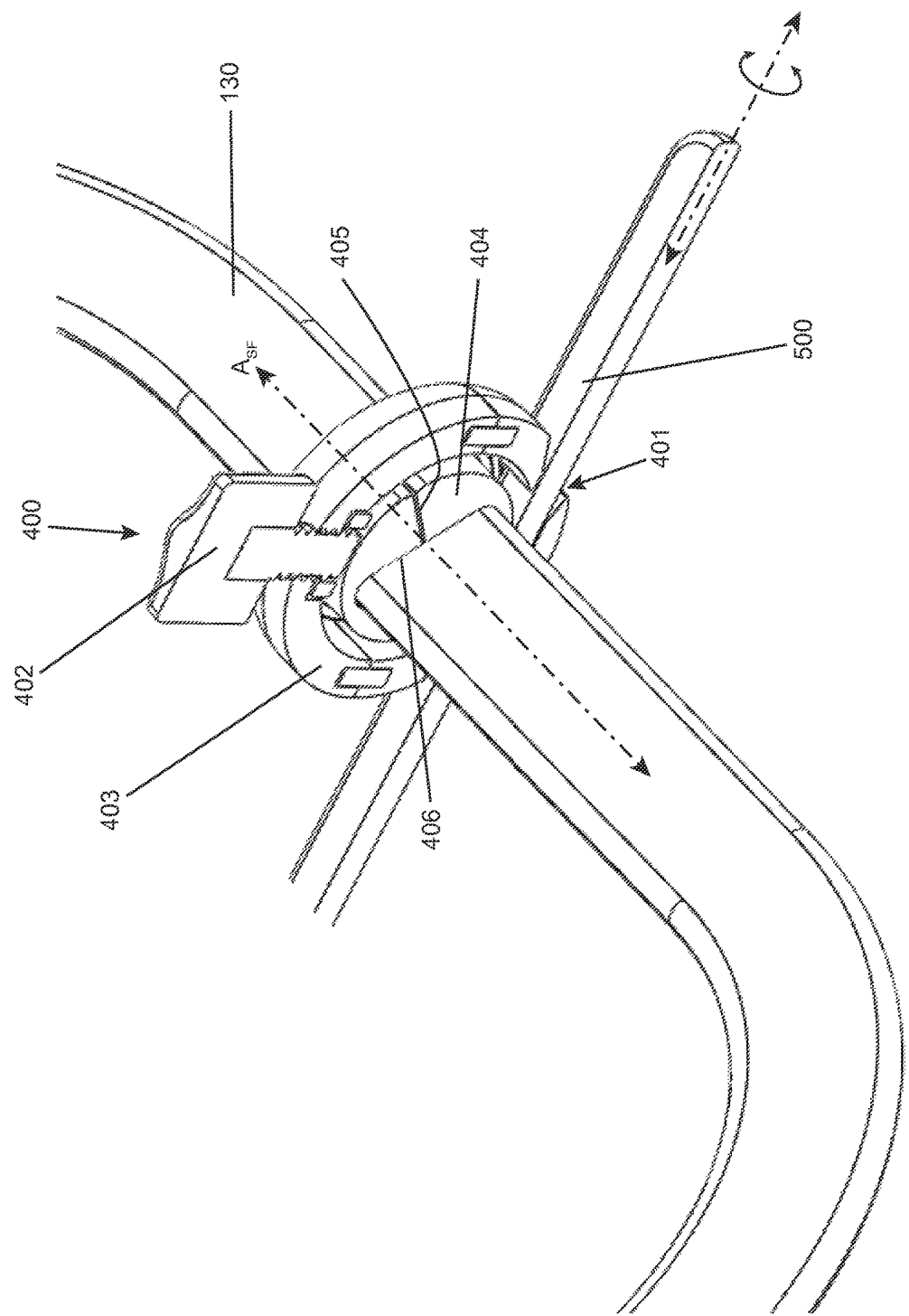
FIG. 7 is a perspective cutaway view of a tool holder positioned on a support frame, in accordance with embodiments of the present inventive concepts.

Each tool holder 400 includes a set screw 402 (e.g. set screws 402a and 402b shown), which can be tightened to lock each tool holder 400 to main support frame 130', for example as described herebelow in reference to FIG. 7. Set screws 402 can comprise a set screw with approximately 8-32 or 10-24 threads. In a loosened state of set screw 402, at least a portion of each associated tool holder 400 rotates about segment of main support frame 130' (e.g. rotates about an axis ASF that is proximate the current position of tool holder 400 as shown). In some embodiments, tool holder 400 is configured to rotate at least 360° about main support frame 130'. In other embodiments, tool holder 400 is configured to rotate less than 360°, such as a rotation less than 180° or less than 90°. Alternatively or additionally, in a loosened state of set screw 402, each associated tool holder 400 can slidingly translate along main support frame 130'. In some embodiments, each set screw 402 can be further configured to lock in place an elongate member (e.g. shaft portions 500a or 500b described herebelow) passing through the associated passageway 401, also for example as described herebelow in reference to FIG. 7.

In the embodiment of FIG. 6, a shaft portion 500a has been positioned within passageway 401a of tool holder 400a, and shaft portion 500b has been positioned within passageway 401b of tool holder 400b. Shaft portion 500a can comprise a tool guide (e.g. a hollow tube) used to support the shaft or other elongate portion of one or more tools, such as one or more of the surgical tools described hereabove. Alternatively, shaft portion 500a can comprise the shaft of a tool (e.g. one or more of the surgical tools described hereabove), wherein passageway 401a provides guiding and fixed orientation support to the inserted tool shaft. Shaft portion 500b is a shaft segment of cheek retractor 150, such that tool holder 400b allows positioning of cheek retractor 150. As described above, loosening of set screws 402a and 402b can allow repositioning relative to main support frame 130' (e.g. repositioning of the associated tool holder 400) of shaft portions 500a and 500b, respectively. Alternatively or additionally, loosening of set screws 402a and 402b can allow repositioning relative to the associated passageway 401 (e.g. sliding and/or rotating within the associated passageway 401) of shaft portion 500a and shaft portion 500b (i.e. cheek retractor 150), respectively. In some embodiments, shaft portion 500 is configured to rotate at least 360° within passageway 401. In other embodiments, shaft portion 500 is configured to rotate less than 360°, such as a rotation less than 180° or less than 90°.

In alternate embodiments, set screw 402 comprises a first set screw used to position and lock a tool holder 400 relative to main support frame 130', and a second set screw used to position and lock an elongate member within passageway 401, dual set screw configuration not shown but configured to allow an operator to independently lock tool holder 400 and an elongate member positioned within passageway 401.

In some embodiments, passageway 401 comprises a first passageway configured to slidingly receive a first elongate member and a second passageway configured to receive a second elongate member, dual passageway configuration not shown but configured to support two elongate members with similar or dissimilar cross sectional geometries. In these embodiments, separate set screws 402 can be used to fix the position of the associated elongate members within each passageway 401.

Oral retractor 100' can comprise a tooth engaging member, or jaw support 160' as shown in FIG. 6, which may be configured to make contact and frictionally engage with the one or more of the patient's teeth (e.g. one or more of the patient's front teeth), such as to stabilize oral retractor 100' relative to the patient. Jaw support 160', or tooth engaging member, can be fixed and/or attachable to main support frame 130'. In some embodiments, jaw support 160' comprises a set screw, not shown but configured to selectively fix jaw support 160' to main support frame 130' (e.g. to allow translation and/or rotation of jaw support 160' relative to main support frame 130'). In some embodiments, jaw support 160 comprises a rigid portion and a more flexible portion, such as a flexible portion (e.g. a soft plastic or gauze) that makes contacts with the patient's teeth and/or gums.

Oral retractor 100' can comprise tongue depressor assembly 140' as shown. Tongue depressor assembly 140' can attach to articulation assembly 200 in a similar fashion to the attachment of tongue depressor blade 140 and articulation assembly 200 described hereabove in reference to FIG. 1. Articulation assembly 200 includes a rotational positioning knob 125, a height positioning knob 126, and an angular positioning knob 127 for articulating the tongue depressor blade 140 in accordance with one or more degrees of freedom. A knob extension similar to or the same as tool 175 can be positioned about one or more knobs so that a user can rotate the corresponding knob from a distance away from the articulation assembly 200.

Tongue depressor assembly 140' includes tongue depressor blade 140, which can comprise one or more attachable tongue depressor blades such as are described hereabove in reference to FIG. 3. In some embodiments, tongue depressor assembly 140' comprises five or more, or seven or more different tongue depressor blades 140 which can be operably attached to oral retractor 100'. Each tongue depressor blade 140 can comprise a length between 50 mm and 120 mm. In some embodiments, one or more tongue depressor blade can comprise a length of approximately 150 mm, 170 mm or 200 mm. For example, the blade 140 can be a mandible blade having a length of 50-80 mm and width of about 32 mm. Other blades can equally apply such as a laryngeal blade, depending on the procedure performed using the retractor 100'.

Tongue depressor assembly 140' can further include a tube 145 along at least a portion of its length (e.g. along at least a portion of the length of tongue depressor blade 140). In some embodiments, tube 145 is attachable to one or more tongue depressor blades 140, such as via one or more connecting elements, not shown but such as mating snaps or mating projections and grooves. Tube 145 can comprise a fluid attachment port, port 146, which can be constructed and arranged to operably attach to a vacuum and/or irrigation line. Tube 145 can comprise one or more openings, holes 147. Tube 145 and holes 147 can be constructed and arranged to provide and/or remove one or more fluids (e.g. liquids or gases) from and/or to an irrigation and/or vacuum source, respectively. In some embodiments, tube 145 comprises two or more lumens, such as two or more lumens which connect to similar and/or different holes 147.

In some embodiments, tongue depressor assembly 140' can comprise functional element 148, such as one or more sensors or transducers positioned on or near a surface of tongue depressor 140. Alternatively or additionally, one or more functional elements 148 can be positioned on or near fluid attachment port 156 and/or tube 145. Functional element 148 can comprise a sensor selected from the group consisting of: a pressure sensor; a smoke sensor; a pH sensor; a blood gas sensor; blood glucose sensor; a respiration sensor; an EEG sensor; a temperature sensor; an electrode; and combinations of these. Alternatively or additionally, functional element 148 can comprise a transducer selected from the group consisting of: a light; an infrared light; a visible light; a radioactive element; an ultrasound delivery element; an electrode; a camera; and combinations of these.

FIG. 7 is a perspective cutaway view of a tool holder positioned on a support frame, in accordance with embodiments of the present inventive concepts. Tool holder 400 has been positioned about main support frame 130 as shown, and includes set screw 402 and passageway 401 as described hereabove in reference to FIG. 6. Tool holder 400 can be permanently attached to main support frame 130, or tool holder 400 can be configured for operator attachment and/or removal from main support frame 130, such as is described herebelow in reference to FIG. 8. Tool holder 400 comprises an outer housing, shell 403, of construction and arrangement to relatively maintain its shape (e.g. not deform) during use. Rotatably positioned within shell 403 is an inner housing, cam 404. Cam 404 can be constructed and arranged such that one or more portions of cam 404 compress or otherwise change shape during use, such as is described herebelow. Cam 404 can comprise one or more compressible materials (e.g. an elastomeric material) and/or cam 404 can comprise one or more compressible slots or other shape-changing recesses (e.g. slots 405 shown) constructed and arranged to allow tool holder 400 to compress about and frictionally engage main support frame 130 and/or an shaft portion 500. Passageway 401 can comprise a lumen passing through shell 403, as shown. Alternatively or additionally, passageway 401 can comprise a lumen passing through cam 404. Alternatively or additionally, passageway 401 can comprise a separate tube, not shown but such as one or more hollow tubes attached to shell 403 and/or cam 404.

Tool holder 400 and cam 404 can be constructed and arranged such that tightening of set screw 402 performs at least two functions. A first function can include fixing the position of tool holder 400 about main support frame 130, by compressing a portion of cam 404 about main support frame 130 (e.g. as slot 405 narrows). Another function can include fixing the position of shaft portion 500 relative to tool holder 400, by capturing shaft portion 500 within passageway 401, due to a deflection of a portion of cam 404 into passageway 401 such that cam 404 frictionally engages shaft portion 500. Another function can include fixing the angular rotation (i.e. preventing rotation) of cam 404 relative to shell 403. Loosening of set screw 402 can reverse one or more functions, such as to allow translation and/or rotation of tool holder 400 about main support frame 130 and/or translation and/or rotation of shaft portion 500 within passageway 401.

Figure 8:
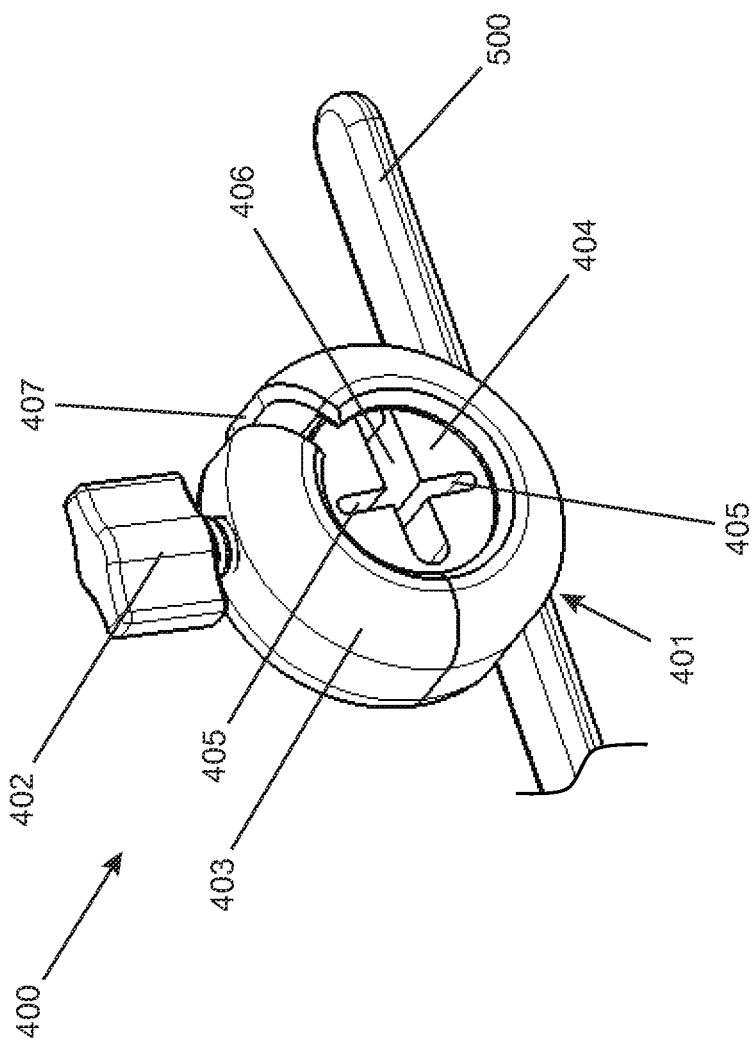
FIG. 8 is a perspective view of a tool holder into which an elongate member has been inserted, in accordance with embodiments of the present inventive concepts.

FIG. 8 is a perspective view of a tool holder 400 into which a shaft portion 500 has been inserted, in accordance with embodiments of the present inventive concepts. Tool holder 400 includes passageway 401, and shaft portion 500 is positioned within passageway 401. Tool holder 400 further includes shell 403, cam 404 and set screw 402. Passageway 401, shell 403, cam 404 and set screw 402 can be of similar construction and arrangement to shell 403 and cam 404 of FIG. 7. Shell 403 of FIG. 8 further includes access slot 407, configured to allow an operator to laterally attach tool holder 400 to a support frame, such as support frames 130 and 130' described hereabove. Tool holder 400 can be oriented such that a segment of a support frame passes through slot 407, and engages slot 406 of cam 404. Slot 406 can comprise a non-circular shape, such as the oval shape shown, such as to limit or prevent rotation of cam 404 relative to main support frame 130. Cam 404 can further include one or more slots 405 as shown, each configured to allow cam 404 to compress about inserted frame 130.

FIG. 9 is a view of a system including a robotically manipulatable tool holder 400', in accordance with embodiments of the present inventive concepts. Tool holder 400' can be operatively attached to a support frame, such as support frames 130 and/or 130' described hereabove. Tool holder 400' comprises shell 403 and cam 404. Shell 403 and cam 404 can be of similar construction and arrangement to shell 403 and cam 404 of FIG. 7. Shell 403 can include slot 407 which is constructed and arranged to allow a user to laterally apply tool holder 400' about a support frame to engage the support frame with slot 406. Cam 404 can include one or more compression-enabling slots, such as slots 405 shown. Tool holder 400' further comprises passageway 401 which is configured to receive a shaft portion 500, such as has been described hereabove.

Tool holder 400' can include one or more robotically controlled motion transfer assemblies configured to reposition tool holder 400' about a frame or reposition shaft portion 500 relative to tool holder 400'. Tool holder 400' can comprise motor 414a and gear 412a which is operably attached to motor 414a via axle 413a. Motor 414a is fixedly attached to shell 403. Gear 412a operatively engages teeth 411a of cam 404 such that rotation of gear 412a by motor 414a via axle 413a causes shell 403 to rotate about cam 404 (e.g. in one or both directions). Motor 414a is attached to cable 416a, which in turn can be attached to controller 12, such that controller 12 can selectively apply power to motor 414a. Controller 12 can be constructed and arranged similar to controller 12 of FIG. 5 hereabove, such as when controller 12 is connected to a human interface device allowing robotic control of the rotation of shell 403 relative to cam 404 (e.g. to rotate tool holder 400' about a frame).

Tool holder 400' can comprise motor 414b and gear 412b which is operably attached to motor 414b via axle 413b. Motor 414b is fixedly attached to shell 403. Gear 412b operatively engages teeth 411b of shaft portion 500 such that rotation of gear 412b by motor 414b via axle 413b causes shaft portion 500 to translate within passageway 401. Motor 414b is attached to cable 416b, which in turn can be attached to controller 12, such that controller 12 can selectively apply power to motor 414b. Controller 12 can be connected to a human interface device allowing robotic control of the translation of shaft portion 500 within passageway 401.

Tool holder 400' can comprise one or more motors 414c (two shown) and associated gears 412c, each of which operably attach to a motor 414c via an axle 413c. One or more gears 412c each operably (e.g. frictionally) engage the surface of a frame positioned within slot 406, such that rotation of a gear 412c by a motor 414c via an axle 413c causes tool holder 400' to translate along the frame (e.g. in one or two directions). Each motor 414c can each be attached to a cable 416c, each of which in turn can be attached to controller 12, such that controller 12 can selectively apply power to each motor 414c. Controller 12 can be connected to a human interface device allowing robotic control of the translation of tool holder 400' along the frame.

Tool holder 400' can comprise an actuator 415 configured to selectively apply a force to cam 404, similar to the force applied to cam 404 by set screw 402 described hereabove in reference to FIG. 7. Actuator 415 can comprise a component selected from the group consisting of: a solenoid; a linear drive assembly; a hydraulic piston; a pneumatic piston; a shaped memory component; and combinations of these. Application of the force to cam 404 by actuator 415 can perform one or two functions, simultaneously or sequentially. Application of force to cam 404 by actuator 415 can cause cam 404 to frictionally engage a support frame positioned within slot 406, such as main support frame 130 or 130' described hereabove. Alternatively or additionally, application of force to cam 404 by actuator 415 can cause cam 404 to deflect within a portion of passageway 401, such as to frictionally engage (e.g. lock) shaft portion 500 within passageway 401 (e.g. to prevent rotation and/or translation of shaft portion 500). Actuator 415 can be attached to controller 12 via cable 416d.

Motors, 414a, 414b and/or 414c can comprise a motor selected from the group consisting of: AC motor; DC motor; stepper motor; and combinations thereof. Gears 412a and 412b can comprise worm gears. Gears 412c can comprise frictionally engaging drive wheels.

While the tool holders 400 and 400' described in reference to FIGS. 6-9 have been described for attaching to main support frames 130 and 130' of the present inventive concepts, it should be understood that attachment to any rigid or semi-rigid structure can be performed. Tool holders 400 or 400' can include an attachment portion (e.g. slots 106 and/or 107 described hereabove) which is sized to attach to a stabilized elongate portion of any medical support or other medical device.

Tool holders 400 and 400' can be configured to be sterilized one or more times, such as to allow reuse with multiple patients. In some embodiments, one or more components of tool holders 400 or 400' is configured for single use (disposable), while other components are configured for multiple uses (e.g. resterilizable).

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following at least one of the preceding claims.

What is claimed is:
1. An oral retraction device, comprising:
   a tongue depressor blade;
   an articulation assembly constructed and arranged to articulate the tongue depressor blade;
   a support arm constructed and arranged to provide a stabilizing force to the articulation assembly during articulation of the tongue depressor blade; and
   an axle that extends along a sagittal axis, wherein the tongue depressor blade rotates about the sagittal axis,
   wherein the articulation assembly is constructed and arranged to at least rotate the tongue depressor blade about the sagittal axis relative to the support arm, wherein the articulation assembly comprises a first portion and a second portion in communication with the first portion, wherein the first portion extends above a top surface of the support arm, wherein the first and second portions rotate together relative to the support arm,
   wherein the articulation assembly includes a multi-axis gear assembly comprising plurality of gears that articulate the tongue depressor blade in at least three degrees of freedom,
   wherein the plurality of gears includes at least one of a rotational positioning gear, a height positioning gear, or an angular positioning gear,
   wherein the tongue depressor blade comprises a set of geared teeth configured to frictionally engage a gear of the multi-axis assembly coupled to an axle that extends along an axis,
   wherein the height positioning gear engages the geared teeth and drives an articulation of the tongue depressor blade in a linear direction with a single degree of freedom along the sagittal axis for adjusting an insertion length of the tongue depressor blade.

2. The oral retraction device of claim 1, wherein the oral retraction device is capable of being positioned in a mouth region of a patient, and is constructed and arranged to provide access via the mouth region to an interior region of the patient.

3. The oral retraction device of claim 1, wherein the oral retraction device is capable of being positioned in a patient's mouth and a force is applied to the patient's tongue by the tongue depressor blade to provide access to an internal location of the patient during one or more medical procedures.

4. The oral retraction device of claim 1, wherein the tongue depressor blade is removably coupled to the articulation assembly.

5. The oral retraction device of claim 1, wherein the axle extends from the support arm, the first portion positioned about the axle.

6. The oral retraction device of claim 1, wherein the second portion of the articulation assembly is configured to rotate relative to the first portion.

7. The oral retraction device of claim 6, further comprising an angular positioning gear comprising a knob, wherein the knob is configured to act as a stop lock when the second portion rotates about the axle.

8. The oral retraction device of claim 1, wherein the second portion comprises one or more arms configured to abut and slidingly receive the tongue depressor blade via a channel.

9. The oral retraction device of claim 1, wherein the articulation assembly includes a plurality of knobs that engage the plurality of gears.

10. The oral retraction device of claim 1, wherein an engagement of a combination of one or more of the rotational positioning gear, the height positioning gear, and the angular positioning gear permits access to a mouth region of a patient.

11. The oral retraction device of claim 1, wherein the angular positioning gear comprises a knob, and a rotation of the angular positioning gear drives an articulation of the tongue depressor blade in a curvilinear direction with a single degree of freedom about a frontal axis.

12. The oral retraction device of claim 1, further comprising a main support frame coupled to the articulation assembly, wherein the main support frame is coupled to the support arm and linearly translates relative to the support arm.

13. The oral retraction device of claim 1, wherein the rotational positioning gear is coupled to a rotational positioning knob, wherein the rotational positioning knob engages the rotational positioning gear to rotatably engage a gear at a proximal end of the first portion, wherein a rotation of the rotational positioning knob in turn engages the rotational positioning gear and the gear at the proximal end of the first portion, and drives an articulation of the first portion about the axle to at least partially rotate the tongue depressor blade about the sagittal axis.

* * * * *